(12) United States Patent
Orge

(10) Patent No.: US 8,771,216 B2
(45) Date of Patent: Jul. 8, 2014

(54) FLUID COMMUNICATION DEVICE AND METHOD OF USE THEREOF

(75) Inventor: Faruk Orge, Solon, OH (US)

(73) Assignee: University Hospitals of Cleveland, Cleveland, OH (US)

(*) Notice: Subject to any disclaimer, the term of this patent is extended or adjusted under 35 U.S.C. 154(b) by 0 days.

(21) Appl. No.: 12/941,888

(22) Filed: Nov. 8, 2010

(65) Prior Publication Data

US 2013/0165840 A1    Jun. 27, 2013

Related U.S. Application Data

(60) Provisional application No. 61/280,651, filed on Nov. 6, 2009.

(51) Int. Cl.
*A61M 5/00* (2006.01)

(52) U.S. Cl.
USPC .................... 604/8; 604/9; 604/264

(58) Field of Classification Search
USPC .................. 604/8–9, 264
See application file for complete search history.

(56) References Cited

U.S. PATENT DOCUMENTS

| 5,601,094 | A  | * | 2/1997  | Reiss .................. 128/899 |
| 6,254,562 | B1 | * | 7/2001  | Fouere ................. 604/8 |
| 6,638,239 | B1 | * | 10/2003 | Bergheim et al. ........ 604/27 |
| 6,730,056 | B1 | * | 5/2004  | Ghaem et al. .......... 604/9 |
| 6,827,700 | B2 | * | 12/2004 | Lynch et al. ........... 604/8 |
| 7,135,009 | B2 |   | 11/2006 | Tu et al. |
| 7,431,710 | B2 |   | 10/2008 | Tu et al. |
| 2003/0236483 | A1 | * | 12/2003 | Ren .................... 604/8 |
| 2004/0193262 | A1 | * | 9/2004  | Shadduck ............ 623/4.1 |
| 2007/0123812 | A1 | * | 5/2007  | Pinchuk et al. ......... 604/8 |
| 2007/0191863 | A1 |   | 8/2007  | De Juan, Jr. et al. |
| 2008/0183121 | A2 | * | 7/2008  | Smedley et al. ......... 604/8 |

* cited by examiner

*Primary Examiner* — Leslie Deak
(74) *Attorney, Agent, or Firm* — Renner, Otto, Boisselle & Sklar, LLP

(57) ABSTRACT

A fluid communication device is configured to provide fluid flow between first and second chambers separated by tissue. The fluid communication device includes a member configured for insertion through and engagement of the tissue. The member includes a first opening near a first end of the member for fluidic communication with the first chamber and a second opening near a second end of the member for fluidic communication with the second chamber, the fluid member including a fluid passage that provides fluidic communication between the first and second chambers. The fluid communication device is configured to be positioned with the eye to provide fluid communication between an anterior chamber of the eye and Schlemm's canal.

17 Claims, 32 Drawing Sheets

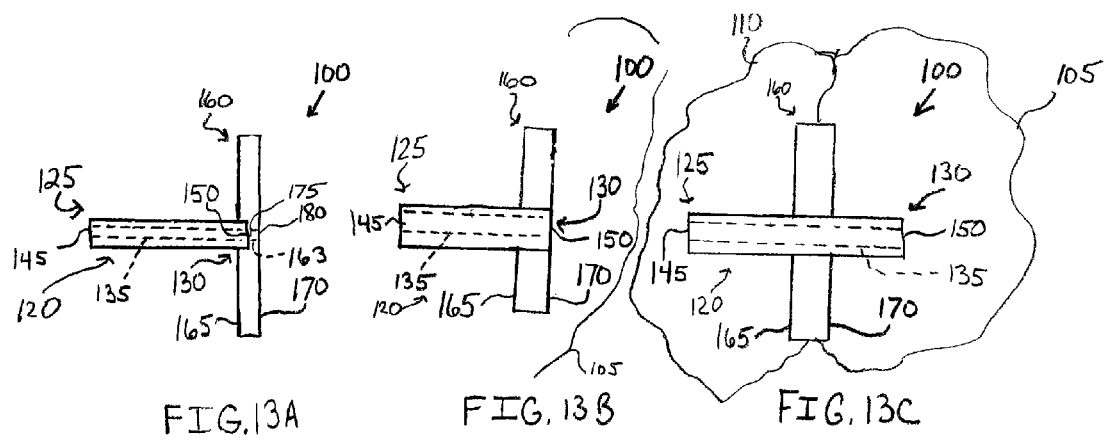

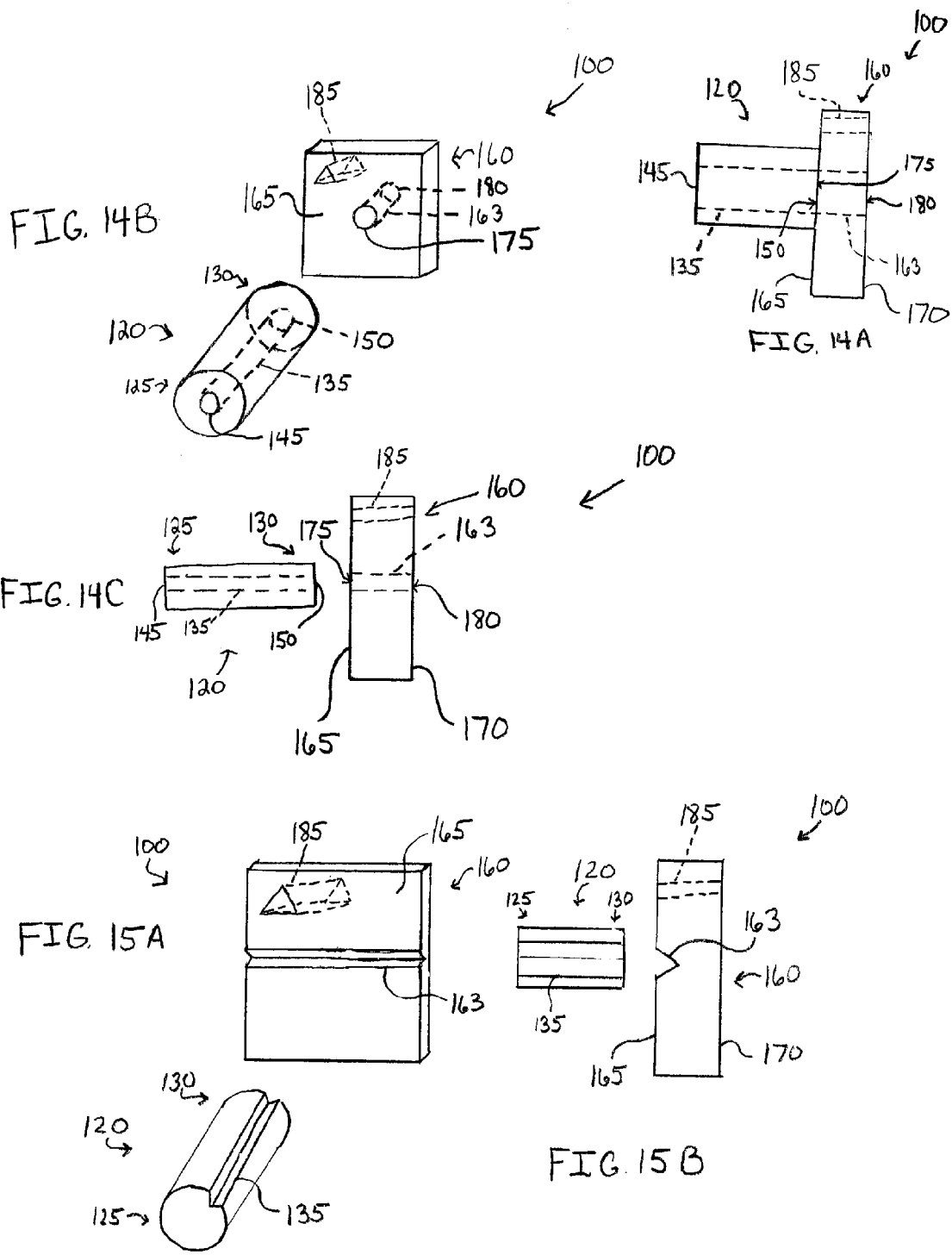

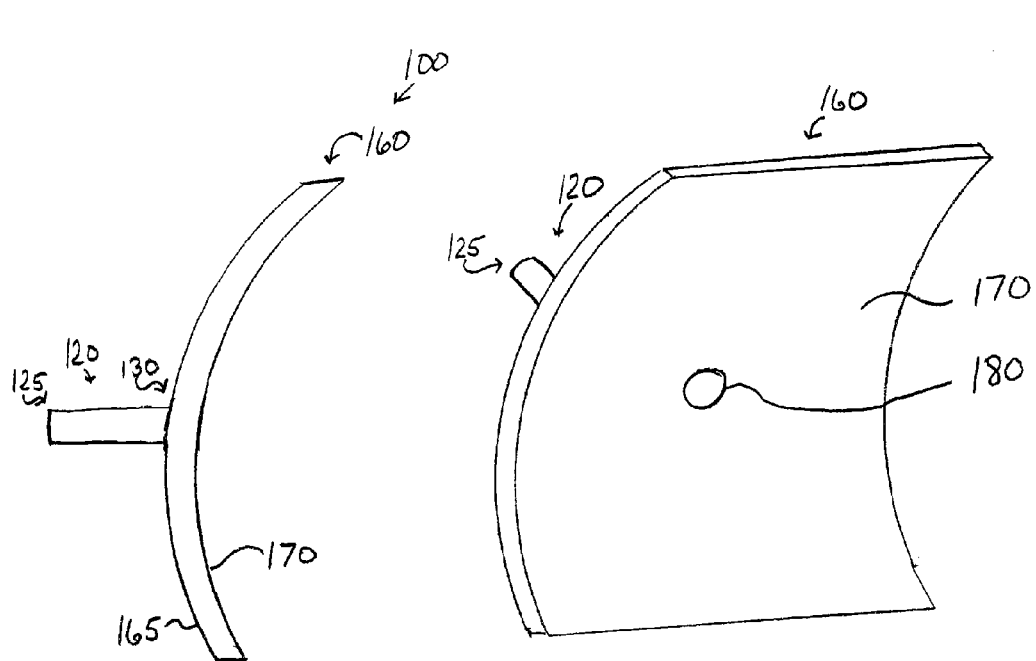
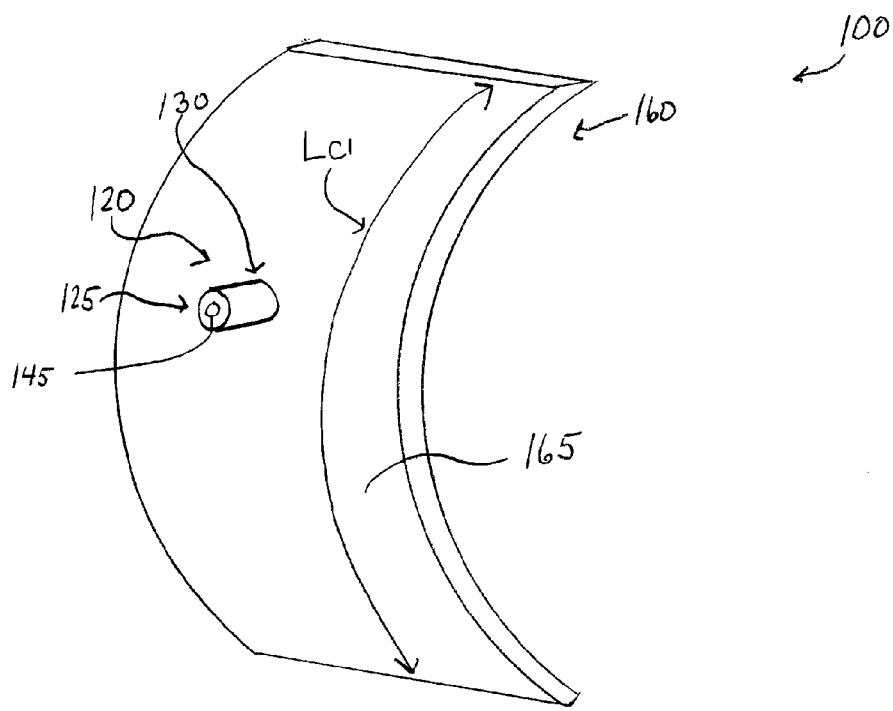

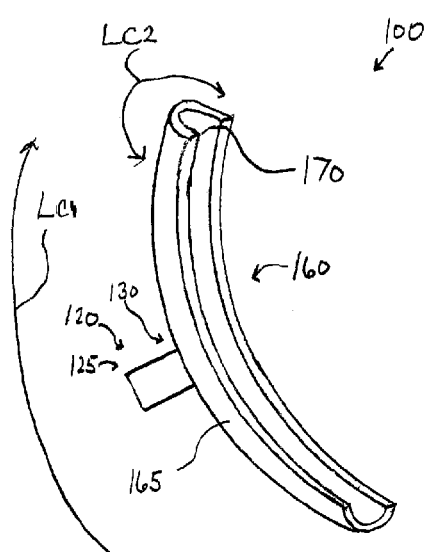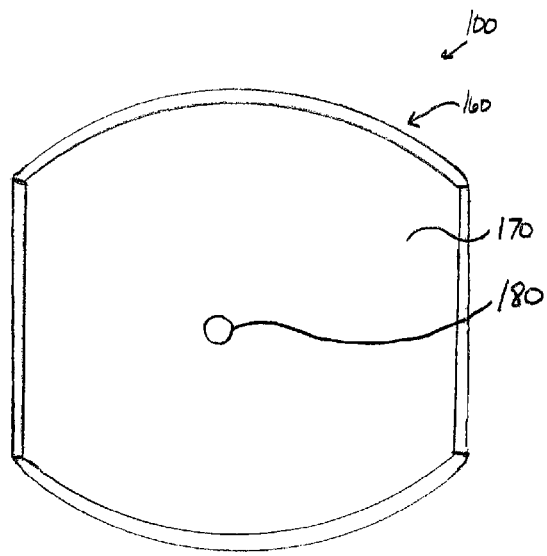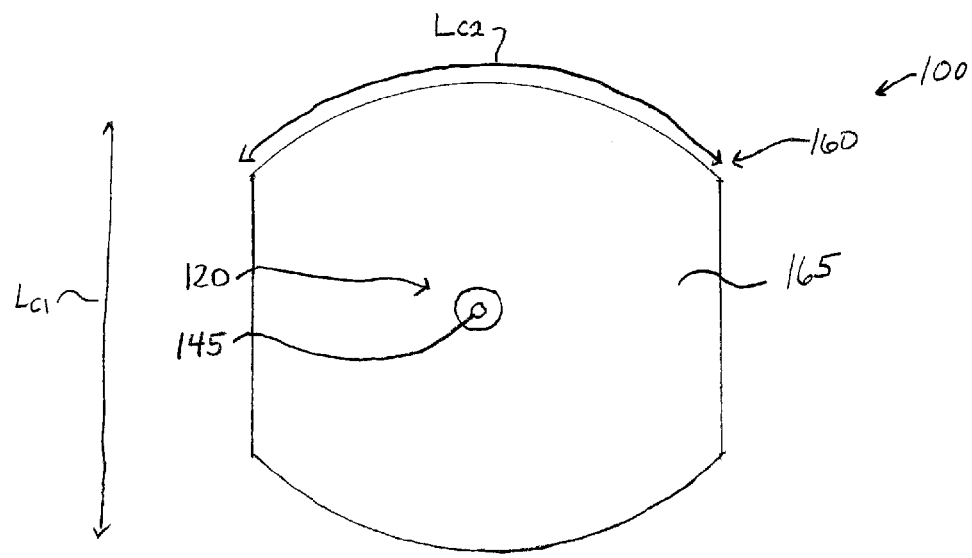
FIG. 18A
FIG. 18B
FIG. 18C

FLUID COMMUNICATION DEVICE AND METHOD OF USE THEREOF

RELATED APPLICATION

This application claims the benefit of U.S. Provisional Application No. 61/280,651, filed Nov. 6, 2009, which is hereby incorporated herein by reference.

FIELD OF THE INVENTION

The present invention generally relates to a fluid communication device, and particularly, to an ocular fluid communication device and method of using thereof.

BACKGROUND

It is estimated that nearly three million people in the United States have glaucoma and more than one hundred thousand people are blind from glaucoma. Glaucoma is the second leading cause of blindness in adult Americans age eighteen to sixty-five and the leading cause of blindness in African Americans.

Glaucoma is an optic neuropathy (a disorder of the optic nerve) that usually occurs in the setting of an elevated intraocular pressure. An increase in intraocular pressure may result in changes in the appearance ("cupping") and function ("blind spots" in the visual field) of the optic nerve. If the pressure remains high enough for a long enough period of time, total vision loss may occur.

The eye is a hollow structure that contains a clear fluid called "aqueous humor." Aqueous humor is continuously produced in the posterior chamber of the eye by the ciliary body. The fluid passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. The primary pathway for aqueous outflow in humans is through the "canalicular" route that involves the trabecular meshwork and Schlemm's canal. The trabecular meshwork and Schlemm's canal are located at the junction between the iris and the cornea called "the angle." The trabecular meshwork is composed of collagen beams arranged in a three-dimensional sieve-like structure and lined with a monolayer of trabecular cells. The outer wall of the trabecular meshwork coincides with the inner wall of Schlemm's canal, which is a tube-like structure that runs around the circumference of the cornea. The aqueous fluid travels through the spaces between the trabecular beams into the Schlemm's canal, through a series of collecting channels that drain from Schlemm's canal and into the episcleral venous system. In a normal situation, aqueous production is equal to aqueous outflow and intraocular pressure remains fairly constant in the 10 to 21 mmHg range. High pressure develops in an eye because of an internal fluid imbalance. In glaucoma, the resistance through the canalicular outflow system is higher than normal causing reduced outflow thereby causing an internal fluid imbalance and resulting in an increased pressure.

In primary open angle glaucoma, the drainage angle formed by the cornea and the iris remains open, but the microscopic drainage channels in the trabecular meshwork are at least partially obstructed. Other forms of glaucoma (such as angle closure glaucoma and secondary glaucomas) involve decreased outflow through the canalicular pathway due to mechanical blockage, inflammatory debris, cellular blockage, etc.

When the drainage system does not function properly, the aqueous humor cannot filter out of the eye at its normal rate. As the fluid builds up, the intraocular pressure within the eye increases. The increased intraocular pressure compresses the axons in the optic nerve, which carries vision from the eye to the brain, and also may compromise the vascular supply to the optic nerve. Damage to the optic nerve is painless and slow and a vision loss can occur before a person is even aware of a problem.

Eye and systemic medications are used to treat open angle glaucoma by decreasing the production of aqueous humor or increasing its drainage from the eye. Surgical treatment may be performed when medication fails to lower the intraocular pressure. For example, surgical procedures are used to either open up the anatomically closed irido-corneal angles or create a new drainage pathway of the aqueous humor outside the eye.

Trabeculectomy is a surgical procedure that creates a pathway for aqueous fluid to escape to the surface of the eye. The anterior chamber is entered beneath the scleral flap and a section of deep sclera and trabecular meshwork is excised. Post-operatively, the aqueous fluid passes through the resulting hole and collects in an elevated space beneath the conjunctiva. The fluid then is either absorbed through blood vessels in the conjunctiva or traverses across the conjunctiva into the tear film. A deficiency of such procedure is that it creates a pathway for bacteria that normally live on the surface of the eye and eyelids to get into the eye.

Another surgical procedure involves the use of an aqueous shunt. A full thickness hole is made into the eye at the limbus, usually with a needle. The shunt is inserted into the eye through this hole and aqueous humor drains out to the surface of the eye. Many complications are associated with aqueous shunts. A thickened wall of scar tissue may resist outflow and limit the reduction in eye pressure. The resulting unrestricted flow through the shunt to the outer surface may result in too low of an intraocular pressure and can damage the eye in different ways that could lead to loss of function and sight. As such shunts are open to the surface of the eye, a pathway is created for bacteria to get into the eye and endophthalmitis can occur.

Laser surgery is a surgical procedure to reduce the intraocular pressure and includes cyclophotocoagulation (reducing the production of aqueous humor by using a laser to freeze the part of the eye that produces aqueous humor), iridotomy (use of a laser to make a hole in the iris to allow fluid to flow more freely in the eye), and trabeculoplasty (use of a laser to create holes in the drainage area of the eye to allow fluid to drain more freely). However, laser surgery is complex and suffers from a variety of deficiencies.

SUMMARY OF INVENTION

In an embodiment, a fluid communication device is provided comprising a member, and a fluid passage extending through at least a portion of the member, where the member is positionable in a tissue separating a first chamber from a second chamber to selectively allow fluid flow from the first chamber to the second chamber via the fluid passage to regulate the pressure of the first chamber. The fluid passage of the member may have a diameter capable of allowing fluid to flow from the first chamber to the second chamber at or above a predetermined pressure in the first chamber to regulate the pressure of the first chamber. The fluid passage of the member may be closed at a first pressure and open at a second pressure higher than the first pressure to allow fluid flow therethrough to regulate the pressure of the first chamber. The tissue may be the trabecular meshwork of the eye, the first chamber may be the anterior chamber of the eye, and the second chamber may be the Schlemm's canal or the suprachoroidal space of the eye.

In an embodiment, a fluid communication device is provided comprising a member having a first end and a second end, a fluid passage extending through at least a portion of the member, and a head extending from the second end and insertable through a tissue separating a first chamber and a second chamber, where the head is dissolvable to place the first chamber and the second chamber in fluid communication with the fluid passage. The fluid passage may extend within at least a portion of the member. The fluid passage may extend along at least a portion of the surface of the member. The head may comprise a dissolvable material. The dissolvable material may include, but is not limited to hydroxyaliphatic carboxylic acids, either homo- or copolymers, such as polylactic acid, polyglycolic acid, polylactic glycolic acid, polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-.epsilon.-caprolactone, polydimethylsiloxane, polyamides, polyvinylpyrollidone, polyvinylalcohol phthallate, waxes such as paraffin wax and white beeswax, natural oils, shellac, zein, and mixtures thereof. The tissue may be the trabecular meshwork of the eye, the second chamber may be the anterior chamber of the eye, and the first chamber may be the Schlemm's canal or the suprachoroidal space of the eye. The tissue may be the trabecular meshwork of the eye, the first chamber may be the anterior chamber of the eye, and the second chamber may be the Schlemm's canal or the suprachoroidal space of the eye. The device may be capable of lowering the pressure of the anterior chamber. The device may be capable of regulating the pressure of the anterior chamber.

In an embodiment, a fluid communication device is provided comprising a body having a convex side shaped for engaging a tissue separating a first chamber and a second chamber, a member having a distal end extending from the convex side, and a fluid passage extending at least a portion of the member, where the distal end is insertable in the tissue to place the first chamber and the second chamber in fluid communication with the fluid passage. The body may have a concave side opposite said convex side. The tissue may be the trabecular meshwork of the eye, the second chamber may be the anterior chamber of the eye, and the first chamber may be the Schlemm's canal or the suprachoroidal space of the eye. The tissue may be the trabecular meshwork of the eye, the first chamber may be the anterior chamber of the eye, and the second chamber may be the Schlemm's canal or the suprachoroidal space of the eye. The convex side may be substantially entirely positioned along the tissue when the member is positioned therein. The convex side may be substantially entirely positioned along the outer surface of the tissue when the member is positioned therein. The device may be capable of lowering the pressure of the anterior chamber. The device may be capable of regulating the pressure of the anterior chamber. The fluid passage of the member may have a diameter capable of selectively allowing fluid to flow from the anterior chamber to the Schlemm's canal or the suprachoroidal space of the eye at or above a predetermined pressure in the anterior chamber to regulate the pressure of the anterior chamber.

In an embodiment, a fluid communication device is provided comprising a body comprising a side having a first length and a second length that intersect at a point on the side, a member having an end extending outwardly from the side a distance less than the first length and less than the second length, the member positionable in a tissue separating a first chamber and a second chamber, and a fluid passage extending at least a portion of the member and capable of being in fluid communication with the first chamber and the second chamber when the member is positioned in the tissue. The side may engage the tissue substantially entirely along the first length when the member is positioned in the tissue. The side may engage the tissue substantially entirely along the second length when the member is positioned in the tissue. The side may be convex. The body may further comprise a concave side opposite the convex side. The first length and the second length may intersect substantially perpendicularly to each other. The first length and the second length may intersect at an angle equal to or greater than about forty five degrees. The first length and the second length may intersect at an angle equal to or greater than about thirty degrees. The first length and the second length may intersect at an angle equal to or greater than about ten degrees. The device may be capable of lowering the pressure of the anterior chamber. The device may be capable of regulating the pressure of the anterior chamber. The fluid passage of the member may have a diameter capable of selectively allowing fluid to flow from the anterior chamber to the Schlemm's canal or the suprachoroidal space of the eye at or above a predetermined pressure in the anterior chamber to regulate the pressure of the anterior chamber.

In an embodiment, a fluid communication device is provided comprising a body, a first member having an end extending a length from the body and a first fluid passage extending at least a portion of the first member, and a second member having an end extending a second length from the body, where the members are positionable in a tissue separating a first chamber and a second chamber to position the first fluid passage in fluid communication with the first chamber and the second chamber, and the end of the second member extends a distance into the second chamber greater than the end of said first member. The second member may further comprise a second fluid passage extending at least a portion of the second member and positionable in fluid communication with the first chamber and the second chamber. The first fluid passage may extend within at least a portion of the first member. The first member may extend a first length from the body and the second member may extend a second length from the body, where the second length is greater than the first length. The first member may extend outward from the body substantially parallel to the second member. The tissue may be the trabecular meshwork of the eye, the second chamber may be the anterior chamber of the eye, and the first chamber may be the Schlemm's canal or the suprachoroidal space of the eye. The tissue may be the trabecular meshwork of the eye, the first chamber may be the anterior chamber of the eye, and the second chamber may be the Schlemm's canal or the suprachoroidal space of the eye.

In an embodiment, a device for fluid communication is provided comprising a body comprising a side having a first length and a second length that intersect at a point on the side, a plurality of members each having an end extending outward from the side and positionable in a tissue separating a first chamber and a second chamber, and a plurality of fluid passages extending at least a portion of the members, where the fluid passages are capable of being in fluid communication with the first chamber and the second chamber when the members are positioned in the tissue. At least two members may extend outward from the side along the first length and at least two members may extend outward from the side along the second length. The first length and the second length may intersect substantially perpendicularly to each other. The first length and the second length may intersect at an angle equal to or greater than about forty five degrees. The first length and the second length may intersect at an angle equal to or greater than about thirty degrees. The first length and the second length may intersect at an angle equal to or greater than about ten degrees. The members may extend from the body substantially parallel to each other. The members extend from the body in at least one row and one column. The fluid passages may extend within at least a portion of the members. The device may further comprise a material secured to at least one of the members, where the material is dissolvable to place the first chamber and the second chamber in fluid communication with the fluid passage of the at least one member. The material may be a bioabsorbable material. The tissue may be the trabecular meshwork of the eye, the second chamber may be the anterior chamber of the eye, and the first chamber may be the Schlemm's canal or the suprachoroidal space of the eye. The tissue may be the trabecular meshwork of the eye, the first chamber may be the anterior chamber of the eye, and the second chamber may be the Schlemm's canal or the suprachoroidal space of the eye. The device may further comprise an anchor extending from at least one of the members and capable of engaging the tissue to prevent removal therefrom. The device may further comprise an anchor extending from the body and capable of engaging the tissue to prevent removal therefrom.

In an embodiment, a fluid communication device is provided comprising a body positionable in a first chamber and comprising a first side for engaging a tissue separating the first chamber and a second chamber, a second side opposite the first side, and a tapered end, a member having an end extending outwardly from the first side and positionable in the tissue, and a fluid passage extending at least a portion of the member to place the first chamber in fluid communication with the second chamber via the fluid passage when the member is positioned in the tissue. The tapered end may be tapered at an angle of less than about eighty degrees. The tapered end may be tapered at an angle of less than about sixty degrees. The tapered end may be tapered at an angle of less than about forty five degree. The tapered end may be tapered at an angle of less than about thirty degrees. The tapered end may be tapered at an angle of less than about fifteen degrees. The tapered end may extend from the first side to the second side. The tapered end may extend from the second side to the first side. The tissue may be the trabecular meshwork of the eye, the second chamber may be the anterior chamber of the eye, and the first chamber may be the Schlemm's canal or the suprachoroidal space of the eye. The tissue may be the trabecular meshwork of the eye, the first chamber may be the anterior chamber of the eye, and the second chamber may be the Schlemm's canal or the suprachoroidal space of the eye. The tapered end may be capable of maintaining or otherwise reducing disturbances to the natural fluid flow or dynamics of fluid in the anterior chamber In an embodiment, a fluid communication device is provided comprising a body having a first side and a second side opposite the first side, a member having an end extending outwardly a length from the first side and positionable in a tissue separating a first chamber from a second chamber, and a fluid passage extending at least a portion of the member, where the first chamber is in fluid communication with the second chamber via the fluid passage when the member is positioned in the tissue, and where the body has a thickness extending from the first side to the second side less than the length of the member. The thickness of the body may be less than half of the length of the member. The thickness of the body may be less than one quarter the length of the member. The thickness of the body may be less than one fifth the length of the member. The thickness of the body may be less than one sixth the length of the member. The thickness of the body may be less than one tenth the length of the member. The tissue may be the trabecular meshwork of the eye, the second chamber may be the anterior chamber of the eye, and the first chamber may be the Schlemm's canal or the suprachoroidal space of the eye. The tissue may be the trabecular meshwork of the eye, the first chamber may be the anterior chamber of the eye, and the second chamber may be the Schlemm's canal or the suprachoroidal space of the eye. The thickness of the body may be substantially uniform. The body may be substantially hollow.

The foregoing and other features of the invention are hereinafter described in greater detail with reference to the accompanying drawings.

BRIEF DESCRIPTION OF THE DRAWINGS

FIG. 13A is a side view of the device with the member extending into a portion of the body, FIG. 13B is a side view of the device with the member extending through the body, and FIG. 13C is a side view of the device with the member extending through and beyond both sides of the body.

FIG. 14A is a side view of the device with the body, FIG. 14B is an exploded perspective view of the device of FIG. 14A, and FIG. 14C is an exploded side view of the device of 14A.

FIG. 15A is an exploded perspective view of the device with the body, FIG. 15B is an exploded side view of the device of FIG. 15A.

FIG. 17A is a side view of the device having a body curved along the length $L_{C1}$, FIG. 17B is a rear view of the device of FIG. 17A, and FIG. 17C is a frontal view of the device of FIG. 17A.

FIG. 18A is a side view of the device with a body curved along the length $L_{C1}$ and the length $L_{C2}$, FIG. 18B is a rear view of the device of FIG. 18A, and FIG. 18C is a frontal view of the device of FIG. 18A.

DETAILED DESCRIPTION

While the present invention is described with reference to embodiments described herein, it should be clear that the present invention is not limited to such embodiments. Therefore, the description of the embodiments herein is merely illustrative of the present invention and will not limit the scope of the invention as claimed.

Figure 1:
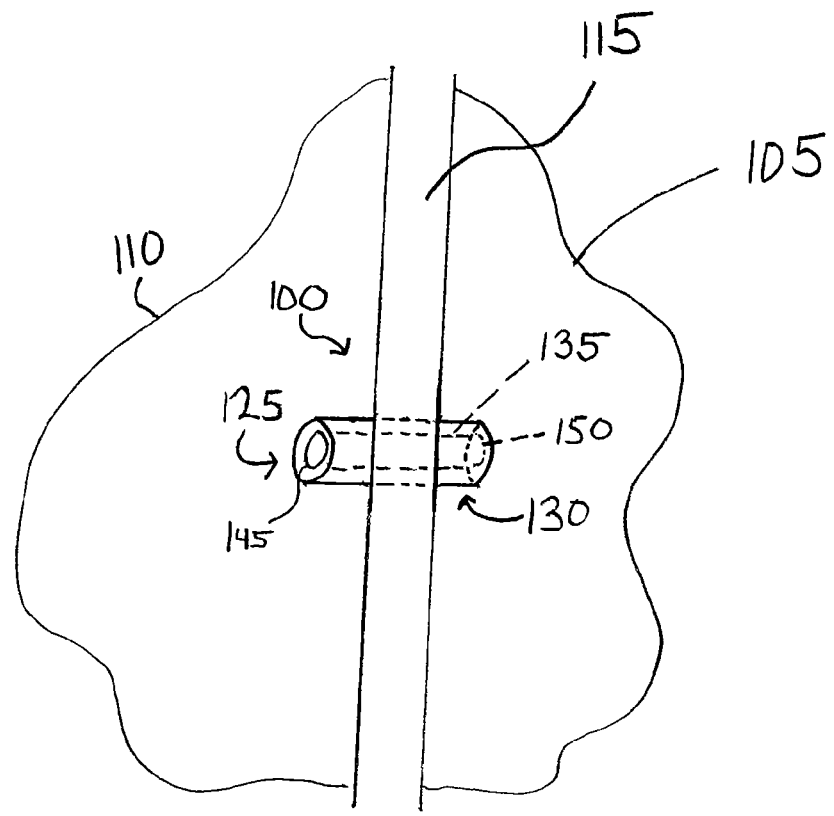
FIG. 1 is a side view of a device providing fluid communication between a first chamber and a second chamber separated by a tissue of a patient.

As shown in FIG. 1, a fluid communication device 100 (hereinafter referred to as the "device 100") is provided for fluid flow or communication (hereinafter referred to as "fluid communication") between a first chamber 105 and a second chamber 110 separated by a tissue 115 of a human or animal (hereinafter referred to as the "patient"). The device 100 is capable of providing or improving fluid communication between the first chamber 105 and the second chamber 110 through non-permeable, blocked, partially blocked, permeable or semi-permeable tissue 115. Although described herein with respect to use in the eye, it is to be understood that the device 100 may be used anywhere in the patient.

Figure 2:
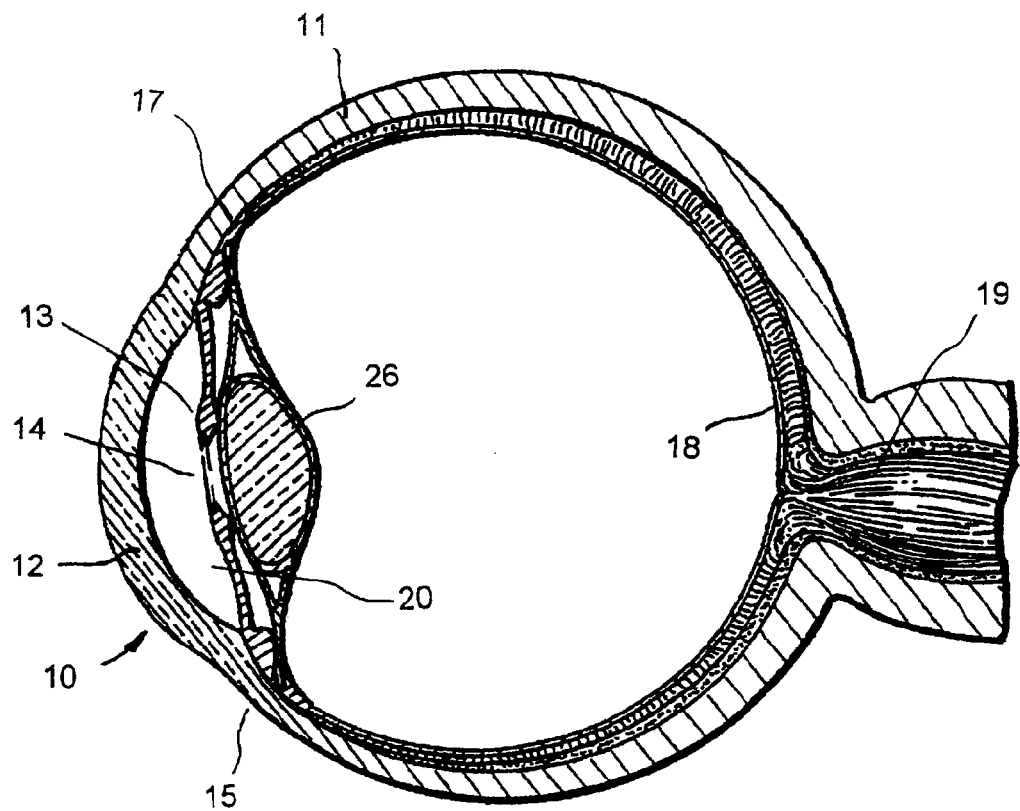
FIG. 2 is a cross-sectional view of an eye.
Figure 3:
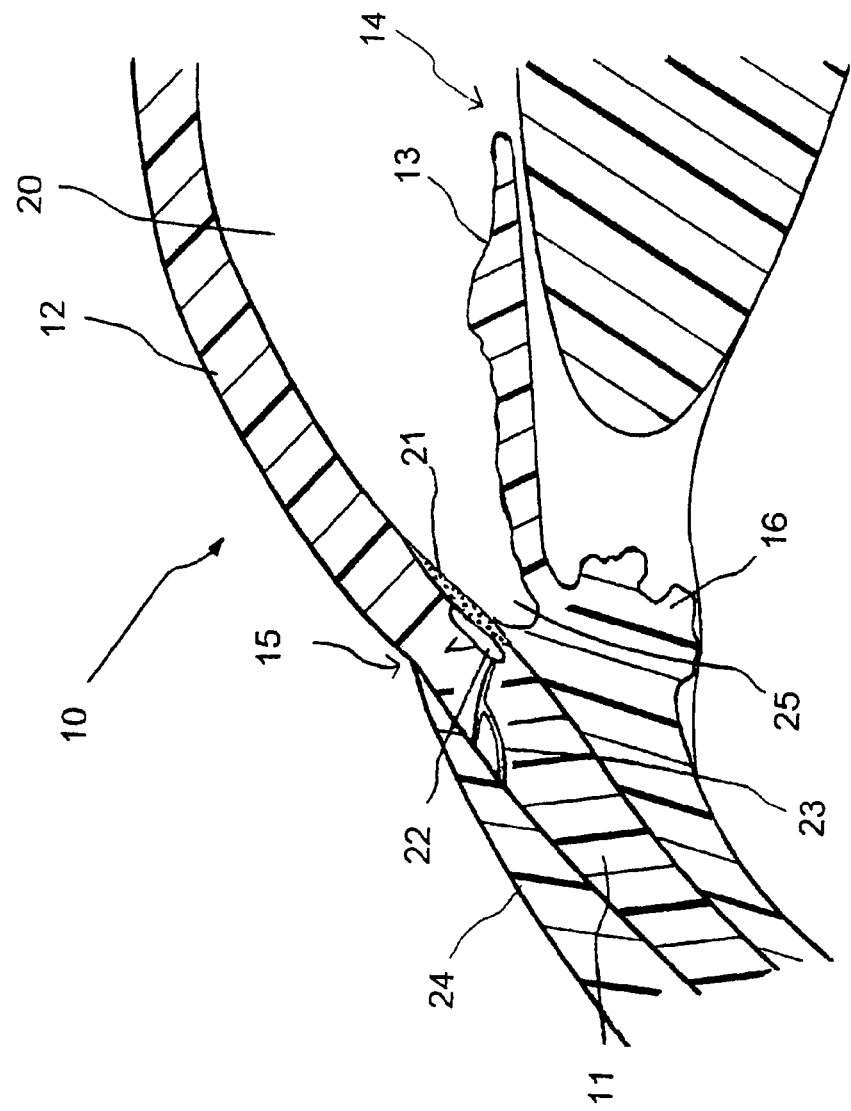
FIG. 3 is an enlarged cross-sectional view of an anterior chamber angle of the eye of FIG. 2.

FIG. 2 shows a sectional view of an eye 10, while FIG. 3 shows a close-up view, showing the relative anatomical locations of the trabecular meshwork, the anterior chamber, and Schlemm's canal. Collagenous tissue known as sclera 11 covers the eye 10 except the portion covered by the cornea 12. The cornea 12 is a transparent tissue that focuses and transmits light into the eye and the pupil 14 which is the circular hole in the center of the iris 13 (colored portion of the eye). The cornea 12 merges into the sclera 11 at a juncture referred to as the limbus 15. The ciliary body 16 begins internally in the eye and extends along the interior of the sclera 11 and becomes the choroid 17. The choroid 17 is a vascular layer of the eye underlying retina 18. The optic nerve 19 transmits visual information to the brain and is sequentially destroyed by glaucoma.

The anterior chamber 20 of the eye 10, which is bound anteriorly by the cornea 12 and posteriorly by the iris 13 and lens 26, is filled with aqueous. Aqueous is a fluid produced primarily by the ciliary body 16 and reaches the anterior chamber angle 25 formed between the iris 13 and the cornea 12 through the pupil 14. In a normal eye, the aqueous is removed through the trabecular meshwork 21. Aqueous passes through trabecular meshwork 21 into Schlemm's canal 22 and through the aqueous veins 23 which merge with blood-carrying veins and into venous circulation. Intraocular pressure of the eye 10 is maintained by the intricate balance of secretion and outflow of the aqueous in the manner described above. Glaucoma is characterized by the excessive buildup of aqueous fluid in the anterior chamber 20 which produces an increase in intraocular pressure.

The device 100 may be positionable or insertable in the trabecular meshwork 21 to provide or improve (collectively "provide") fluid communication between the anterior chamber 20 and the Schlemm's canal 22. The device 100 may allow fluid to flow from the anterior chamber 20 to the Schlemm's canal 22 to decrease or maintain the intraocular pressure of the anterior chamber 20. In a non-limiting example, the device 100 may be provided to regulate the fluid flow from the anterior chamber 20 to the Schlemm's canal to maintain a predetermined intraocular pressure in the anterior chamber 20. Accordingly, the device 100 may allow for the use of existing fluid drainage systems of the patient to regulate the pressure of the anterior chamber 20.

Figure 4:
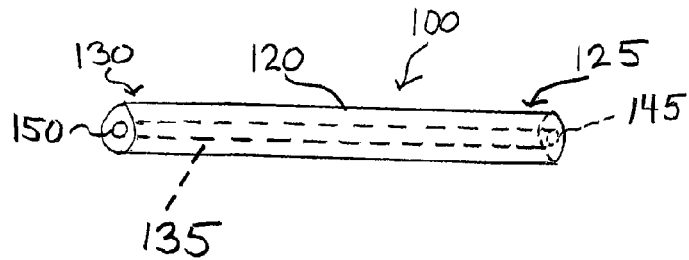
FIG. 4 is a side view of an embodiment of the device.
Figure 5A:
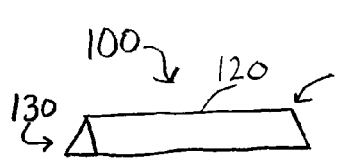
FIGS. 5A, 5B, and 5C are side views of the device with members having different shapes.
Figure 5B:
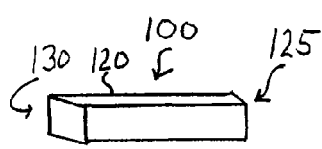

In an embodiment as shown in FIG. 4, the device 100 generally is provided with a member 120 having a first end 125, a second end 130, and a fluid passage 135 (hereinafter referred to as "the passage 135"). Although shown as substantially cylindrical in shape, it is to be understood that the member 120 may be provided in a variety of shapes. Illustrative examples include, but are not limited to, those shown in FIGS. 5A, 5B, and 5C.

The member 120 may comprise materials including, but not limited to, metal, plastic, polymer, composites and combinations thereof. In a nonlimiting example, the member 120 may comprise a biocompatible material including, but not limited to, titanium, titanium alloys, nitinol, medical grade silicone, polyurethane, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and combinations thereof.

It is to be understood that composite biocompatible material may be used, where a surface material may be used in addition to one or more of the aforementioned materials. For example, such a surface material may include polytetrafluoroethylene, polyimide, hydrogel, heparin, therapeutic drugs (such as beta-adrenergic antagonists and other anti-glaucoma drugs, or antibiotics), and the like.

Figure 5C:
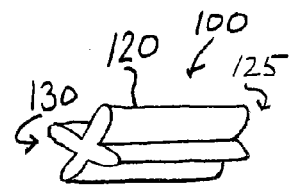
Figure 6A:
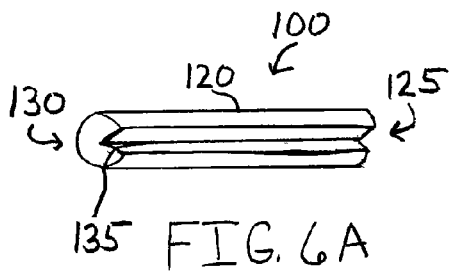
FIG. 6A is a side view of the device with a passage on the outer surface of the member.
Figure 6B:
FIG. 6B is a frontal view of the second end of the device of FIG. 6A.

As shown in FIG. 1, the passage 135 extends at least a portion of the member 120 and is capable of providing fluid communication between the first chamber 105 and the second chamber 110 when the device 100 is positioned in the tissue 115. As shown in FIG. 4, the passage 135 may extend within the member 120 and be in fluid communication with an aperture 145 on the first end 125 and an aperture 150 on the second end 130. As shown in FIGS. 6A and 6B, the passage 135 may extend on the outer surface of the member 120. Although not shown, it is to be understood that the device 100 may be provided with a plurality of passages 135 extending within the member 120, on the outer circumference of the member 120, and combinations thereof. FIG. 5C shows a plurality of circumferentially spaced channels extending longitudinally along the outer surface of the member 120. As shown in FIGS. 7B and 7C, the member 120 may be provided with a plurality of apertures 145, 150, 153 in fluid communication with the passage 135.

The passage 135 may be capable of regulating fluid flow from the anterior chamber 20 to the Schlemm's canal 22 to maintain a predetermined pressure in the anterior chamber 20. In a non-limiting example, a valve (not shown) may be provided in fluid communication with the passage 135 that releases fluid from the anterior chamber 20 to the Schlemm's canal 22 via the passage 135 above a predetermined anterior chamber 20 pressure. In another non-limiting example, the diameter of the passage 135 may be sized to allow for fluid flow from the anterior chamber 20 to the Schlemm's canal 22 above a predetermined anterior chamber 20 pressure. In yet a further non-limiting example, the passage 135 may be collapsible to a first closed position below a predetermined pressure in the anterior chamber 20, and capable of opening to a second position in fluid communication with the anterior chamber 20 and the Schlemm's canal 22 at a pressure in the anterior chamber 20 greater than the predetermined pressure. Accordingly, the pressure of the anterior chamber 20 may be maintained without substantially continuously draining fluid from the anterior chamber 20.

Figure 7A:
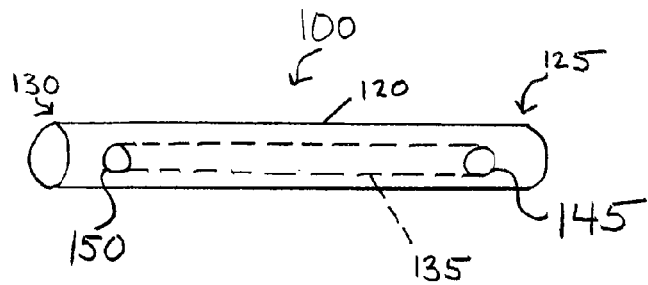
FIG. 7A is a side view of the device with a passage extending a portion of the length of the member.
Figure 7B:
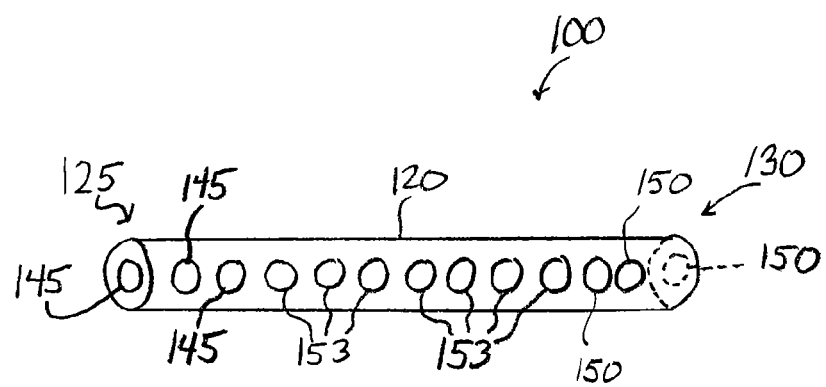
FIGS. 7B and 7C are side views of the device with a plurality of apertures in fluid communication with the passage.
Figure 7C:
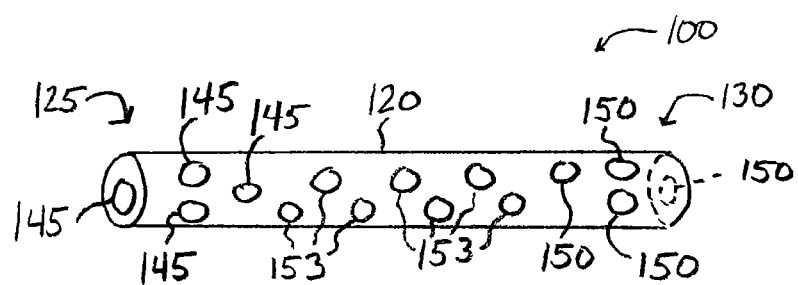
Figure 8:
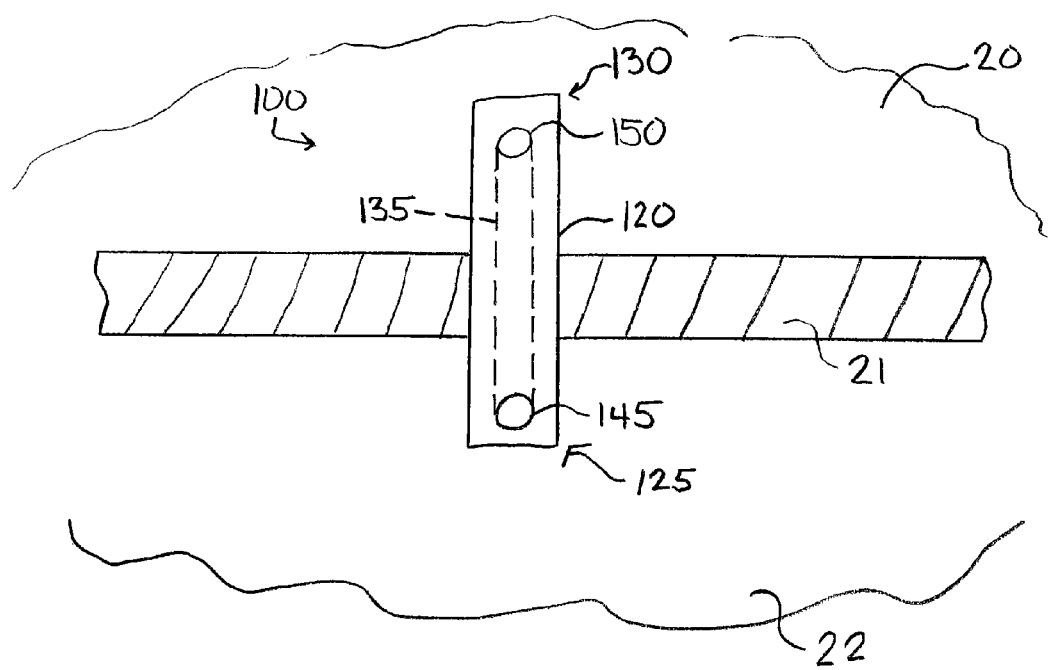
FIGS. 8 and 9 are cross sectional views of the trabecular meshwork having the device positioned therein.
Figure 9:
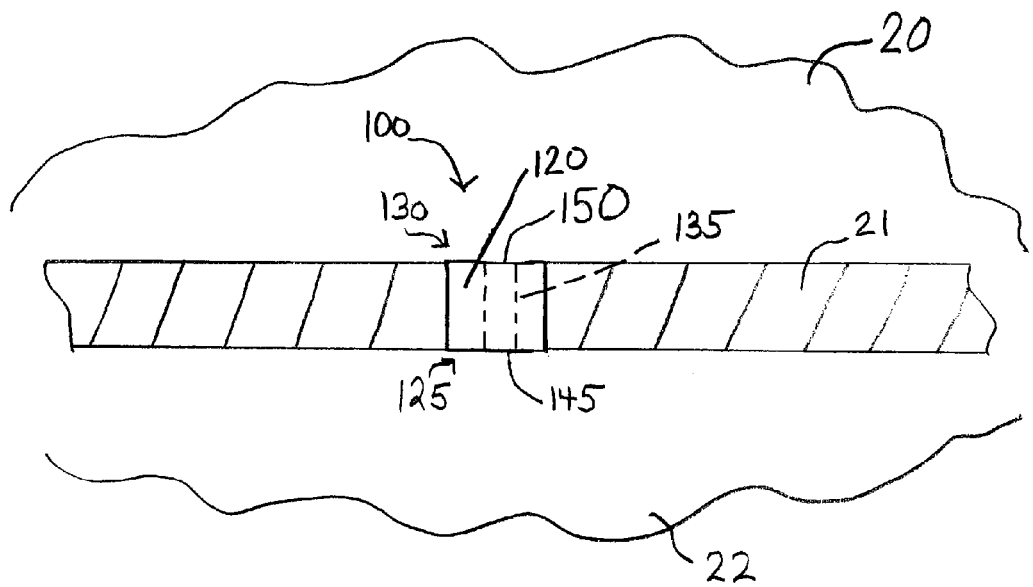

As shown in FIGS. 7A and 8, it is to be understood that the passage 135 may extend only a portion of the length of the member 120. As shown in FIG. 8, the device 100 may be positioned in the trabecular meshwork 21 to place the anterior chamber 20 in fluid communication with the Schlemm's canal 22 via the passage 135 and apertures 145 and 150. As shown in FIG. 9, the first end 125 and the second end 130 do not have to extend beyond the outer surface of the trabecular meshwork 21 to place the anterior chamber 20 in fluid communication with the Schlemm's canal 22 via the passage 135 and apertures 145 and 150. In a non-limiting example (not shown), the first end 125 may extend into the Schlemm's canal and the second end 130 may not extend into the anterior chamber 20. In a non-limiting example (not shown), the second end 130 may extend into the anterior chamber 20 and the first end 125 may not extend into the Schlemm's canal 22.

Figures 10A, 10B, 10C:
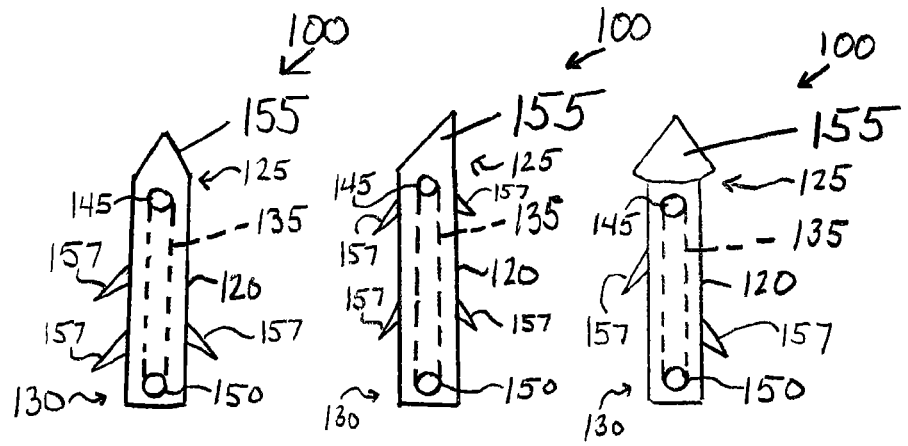
FIGS. 10A, 10B, and 10C are side views of the device with a head.

The first end 125 may be provided with a head 155 shaped to penetrate the tissue 115. In a non-limiting example as shown in FIGS. 10A, 10B, and 100, the head 155 may have a pointed or sharp tip. The head 155 may be secured to or integral with the first end 125. Although not shown, it is to be understood that the head 155 may be provided with one or more apertures in fluid communication with the passage 135.

As shown in FIGS. 10A, 10B and 100, the member 120 may be provided with one or more tissue engagement members 157 (hereinafter referred to as "the tissue engager 157") for securing the device 100 to the tissue 115. The tissue engager 157 may secure the device 100 to prevent misalignment or undesired withdrawal from the tissue 115. Although shown as a barb, the tissue engager 157 may be provided in a variety of forms including, but not limited to, protrusions extending from the member 120, indentations in the member 120, and combinations thereof. In a non-limiting example, as shown in FIG. 10C, the head 155 may extend substantially perpendicularly outward from the member 120 to operate as a tissue engager 157.

The head 155 may be the same material as the member 120. In a non-limiting example, the head 155 may be dissolvable material. In an illustrative example, the head 155 may be a dissolvable material such as a bioabsorbable material or a material capable of absorbing when energy, such as laser or radio frequency energy, is applied thereto. Examples may include, but are not limited to, hydroxyaliphatic carboxylic acids, either homo- or copolymers, such as polylactic acid, polyglycolic acid, polylactic glycolic acid, polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-.epsilon.-caprolactone, polydimethylsiloxane, polyamides, polyvinylpyrollidone, polyvinylalcohol phthallate, waxes such as paraffin wax and white beeswax, natural oils, shellac, zein, and mixtures thereof.

It is to be understood that such dissolvable materials may be used on or in any portion of the device 100. In a non-limiting example, any portion of the device 100 (including internal and external surfaces) may be coated or otherwise plugged with a dissolvable material. In a non-limiting example, apertures 145 and 150, alone or in combination may be coated or otherwise plugged with dissolvable material. In such an example, the passage 135 may be protected from plugging due to disturbances in the tissue, humor, blood or the like, that arise from implantation of the device 100. The dissolvable material may dissolve at a predetermined time after insertion, allowing any disturbances to dissolve, settle, or otherwise filter out of the anterior chamber 20 before fluid flow through the passage 135.

Figures 11A, 11B:
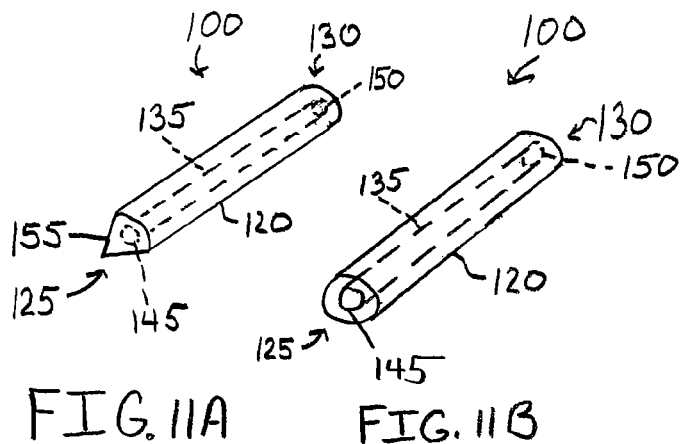
FIGS. 11A and 11B are side views of the device with a dissolvable head.

As shown in FIGS. 11A and 11B, the head 155 may dissolve or otherwise degrade to place the aperture 145 in fluid communication with the Schlemm's canal 22. Although not shown, it is to be understood that the aperture 145, the aperture 150, or any portion of the passage 135, and combinations thereof, may be filled with the dissolvable material. In a non-limiting example, the dissolvable material is capable of preventing the aperture 145, the aperture 150, and the passage 135 from plugging with tissue or other materials when the member 120 is inserted through the tissue 115, such as the trabecular meshwork 21.

In an embodiment, the member 120 may extend from a body 160 that is capable of engaging the tissue 115 when the member 120 is positioned in the tissue 115. Although shown in FIG. 12 as having the member 120 extending substantially perpendicularly outward from the body 160, the member 120 may extend at any angle from the body 160. It is to be understood that the member 120 may be integral with or secured to the body 160 and the body 160 may comprise the same or different material as the member 120.

Figure 12:
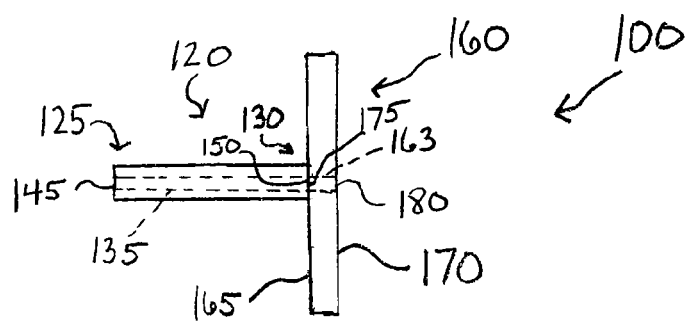
FIG. 12 is a side view of the device with a body.

As shown in FIG. 12, the second end 130 may be secured to a first side 165 of the body 160. As shown in FIG. 13A, the second end 130 may be secured within the body 160. As shown in FIG. 13B, the member 120 may be secured to the body 160 such that the second aperture 150 is in direct fluid communication with the first chamber 105 (the tissue 115 is not shown). In a non-limiting example, as shown in FIG. 13C, the member 120 may be secured to the body 160 and the second end 130 may extend outward from a second side 170 of the body 160 to place the second aperture 150 in direct fluid communication with the first chamber 105 (the tissue 115 is not shown). Although shown in FIG. 13C as having the second end 130 extending substantially perpendicularly outward from the body 160, the second end 130 may extend at any angle from the body 160.

As best shown in FIGS. 14A, 14B, and 14C, the body 160 may be provided with a fluid passage 163 (hereinafter referred to as "the passage 163") for fluid communication with the passage 135. As shown in FIG. 14A and 14B, the passage 163 may be provided with an aperture 180 for fluid communication with the first chamber 105 and an aperture 175 for fluid communication with aperture 150 of the member 120. In a non-limiting example, as shown in FIGS. 14A and 14B, the apertures 150 and 175 (and fluid passages 135 and 163) may be substantially coaxially aligned.

Figure 15C:
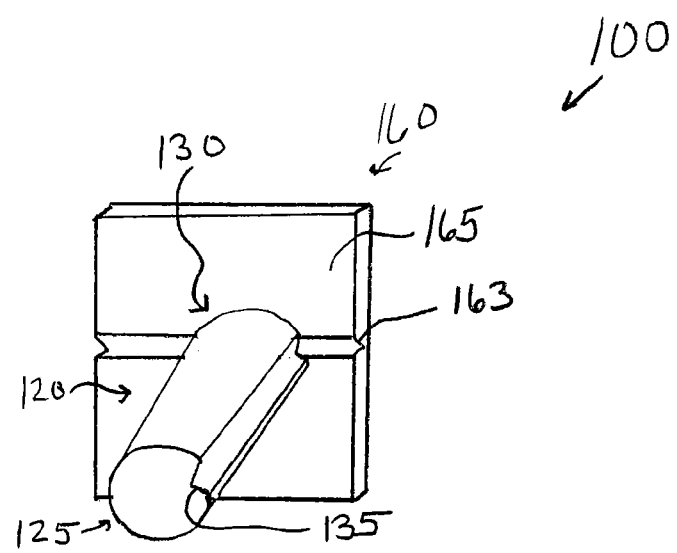
FIG. 15C is a perspective view of the device of FIG. 15A.
Figure 16A:
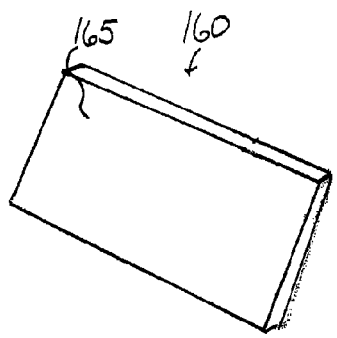
FIGS. 16A, 16B, 16C, 16D, and 16E are perspective views of the body.
Figure 16B:
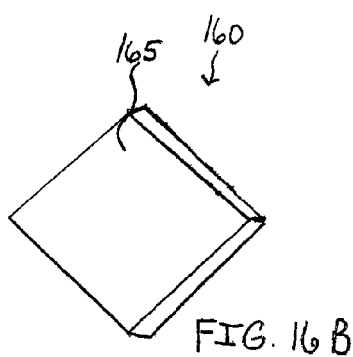
Figure 16C:
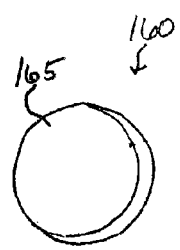
Figure 16D:
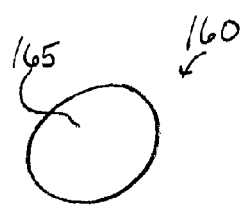
Figure 16E:
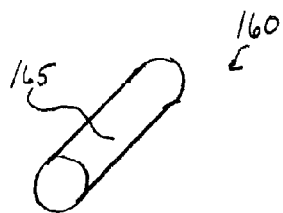
Figures 19A, 19B, 19C:
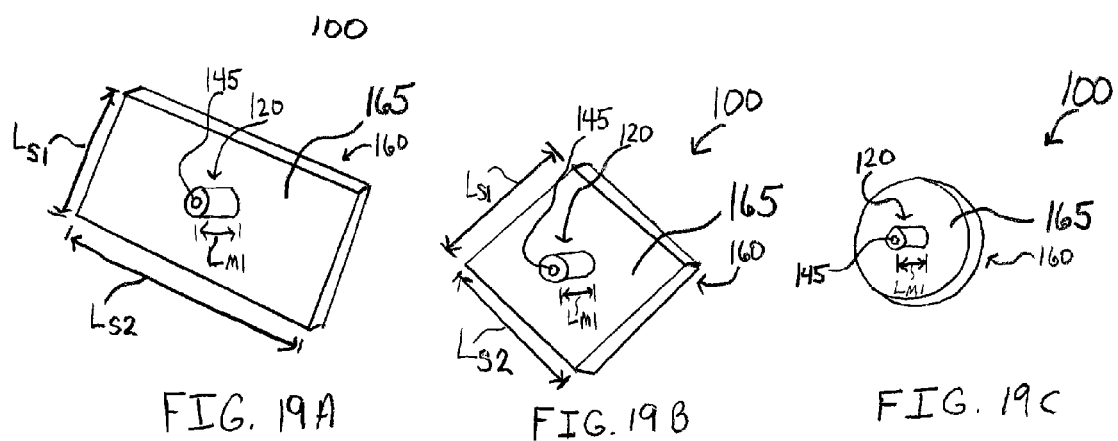
FIGS. 19A, 19B, and 19C are perspective views of the device.
Figure 20:
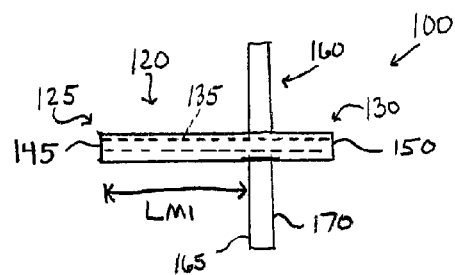
FIG. 20 is a side view of the device.

As shown in FIGS. 15A, 15B, and 15C the passage 163 may be a channel or indentation on the side 165 of the body 160. Although the passage 163, as shown in FIG. 15C, is in fluid communication with the passage 135 (shown as a channel extending along a portion of the outer surface of the member 120), the passage 163 may be in fluid communication with a fluid passage extending within the member 120 (not shown), or combinations thereof. Although not shown, the fluid passage may extend within the member 120 and be in fluid communication with the passage 163, which may be configured to extend along a portion of the side 165, within the body 160, or combinations thereof.

As best shown in FIG. 14B, the body 160 may be have one or more fluid passages 185 extending therethrough. The fluid passage 185 may provide fluid communication between the first chamber 105 or the second chamber 110 and the tissue 115 and may promote tissue ingrowth to further secure the device 100 to the tissue 115. Although not shown, the fluid passage 185 may be in fluid communication with the passage 163.

As shown in FIGS. 16A through 16E, the body 160 may be provided in a variety of shapes, including, but not limited to, rectangles, squares, circles, spheres, and cylinders. In a non-limiting example as best shown in FIGS. 17A, 17B, and 17C, the body 160 may be curved along a length $L_{C1}$ to form a substantially U-shape or C-shape. It is to be understood that the side 165 along length $L_{C1}$ may be shaped to conform to the shape of the tissue 115 to which the side 165 engages when the member 120 is inserted or otherwise positioned in the tissue 115. It is to be understood that the side 165 may engage the tissue along about the entire length $L_{C1}$. In a non-limiting example as best shown in FIGS. 18A, 18B, and 18C, the body 160 may be curved along the length $L_{C1}$ and a length $L_{C2}$ to, for example, form a substantially dish shape on the side 170. It is to be understood that the side 165 along the lengths $L_{C1}$ and $L_{C2}$ may be shaped to conform to the shape of the tissue 115 to which the side 165 engages when the member 120 is inserted or otherwise positioned in the tissue 115. It is to be understood that the side 165 may engage the tissue along about the entire lengths $L_{C1}$ and $L_{C2}$.

Aqueous humor in the anterior chamber 20 is not stagnant and various mechanisms contribute to flow therein, including, but not limited to, gravity, movement and positioning of the patient, movement of the eye 10, temperature differences between the anterior chamber 20 and other parts of the eye 10, fluid flow from the ciliary body 16, and fluid drainage via the trabecular meshwork 21. In an embodiment, the body 160 may be shaped to maintain or otherwise reduce disturbances to the natural fluid flow or dynamics of the aqueous humor in the anterior chamber 20.

Figure 38:
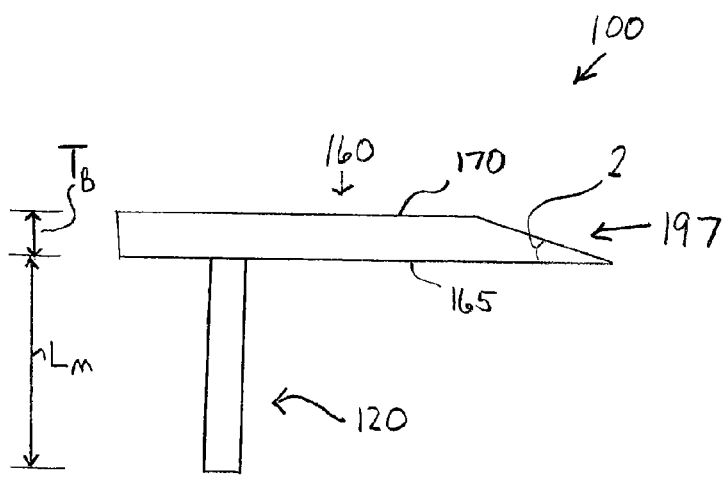
FIG. 38A is an overhead view of the device with a body having a tapered end.
FIG. 38B is an overhead view of the device with a body having a tapered end.
Figure 38:
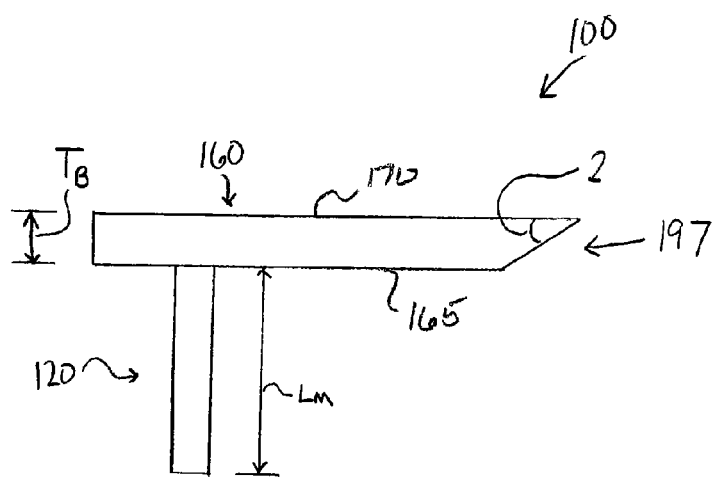

In a non-limiting example, as shown in FIGS. 38A and 38B, an end 197 of the body 160 may be tapered. In an illustrative example, the end 197 may be tapered at an angle α of less about eighty degrees. In yet another illustrative example, the end 197 may be tapered at an angle α of less than about sixty degrees. In a further illustrative example, the end 197 may be tapered at an angle α of less than about forty five degrees. In an illustrative example, the end 197 may be tapered at an angle α of less than about thirty degrees. In yet another illustrative example, the end 197 may be tapered at an angle α of less than fifteen degrees. Although shown as having one tapered end 197, it is to be understood that any or all ends of the body 160 may be tapered.

In an embodiment as shown in FIGS. 38A and 38B, the body 160 may have a thickness $T_B$ of less than the length $L_M$ of the member 120. In another example, the body 160 may have a thickness $T_B$ of less than half the length $L_M$ of the member 120. In yet a further example, the body 160 may have a thickness $T_B$ of less than one quarter the length $L_M$ of the member 120. In yet a further example, the body 160 may have a thickness $T_B$ of less than about one fifth the length $L_M$ of the member 120. In yet a further example, the body 160 may have a thickness $T_B$ of less than about one sixth the length $L_M$ of the member 120.

In an embodiment, as best shown in FIGS. 19A, 19B, 19C and 20, the member 120 may extend from the body 160 a length $L_{M1}$ that is greater than a first length $L_{S1}$ of the side 165, and greater than a second length $L_{S2}$ of the side 165. In a non-limiting example, the length $L_{S1}$ and the length $L_{S2}$ intersect at a point on the side 165 substantially perpendicular to each other.

Figure 21A:
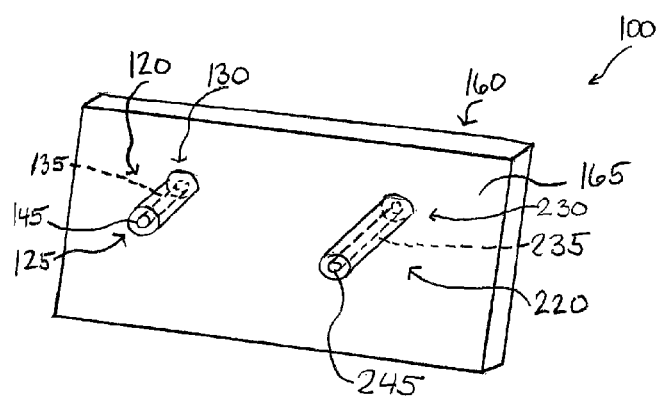
FIG. 21A is a perspective view of the device with a first member having a length different than a second member.
Figure 21B:
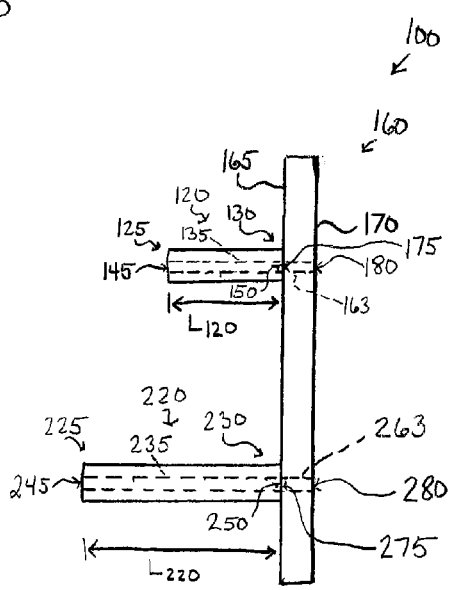
FIG. 21B is an overhead view of the device of FIG. 21A.
Figure 21C:
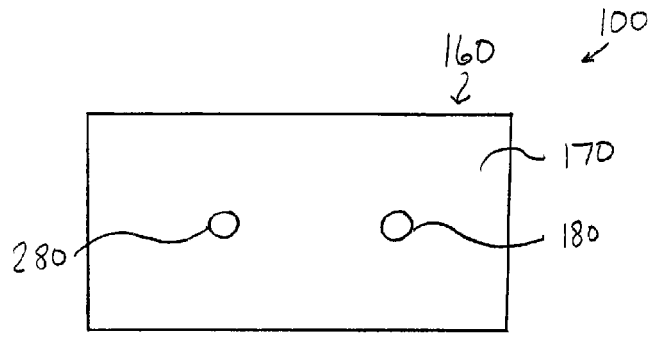
FIG. 21C is a rear view of the device of FIG. 21A.
Figure 33:
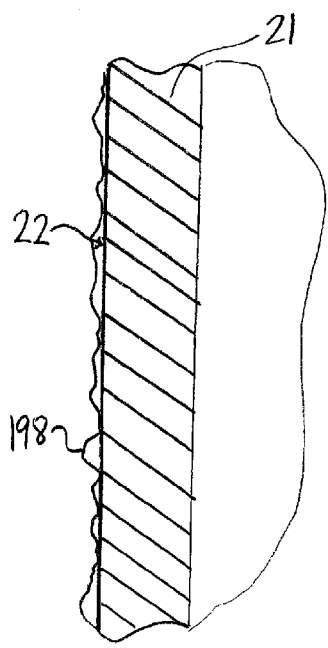
FIG. 33 is a cross sectional view of the trabecular meshwork, Schlemm's canal, and the anterior chamber in which the Schlemm's canal is substantially collapsed.
Figure 34:
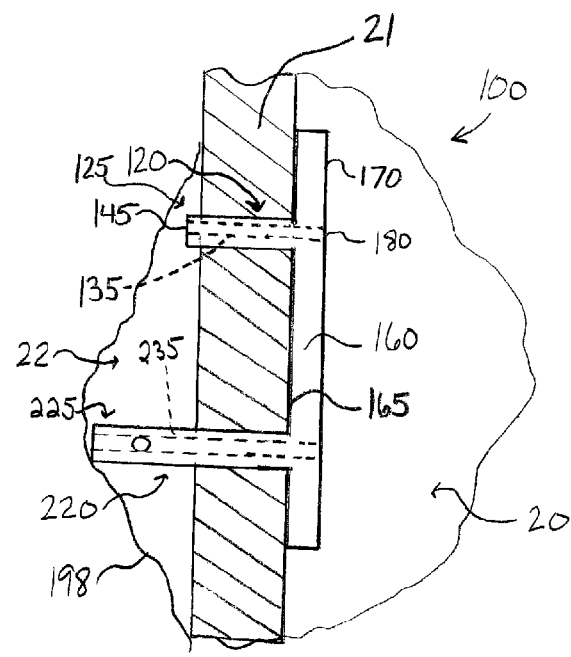
FIG. 34 is a cross sectional view of the trabecular meshwork with the device maintaining the Schlemm's canal in an open position.

In an embodiment, as best shown in FIGS. 21A, 21B, and 21C, the device 100 may be provided with a first member 120 having a length $L_{120}$ extending from the side 165, and a second member 220 having a length $L_{220}$ extending from the side 165 a distance greater than the length $L_{120}$. The second member 220 may be capable of maintaining the Schlemm's Canal 22 in a substantially open position. As shown in FIG. 33, the walls 198 of the Schlemm's canal 22 may collapse against the trabecular meshwork 21 to impede or otherwise prevent fluid flow from the anterior chamber 20 to the Schlemm's canal 22. As best shown in FIG. 34, the first end 225 of the second member 220 may maintain the Schlemm's canal 22 in an open position relative to the first member 120 to allow fluid to flow substantially unimpeded by the walls 198 of the Schlemm's canal 22 from the anterior chamber 20 to the Schlemm's canal 22 via the passage 135 in the first member 120.

Figure 35:
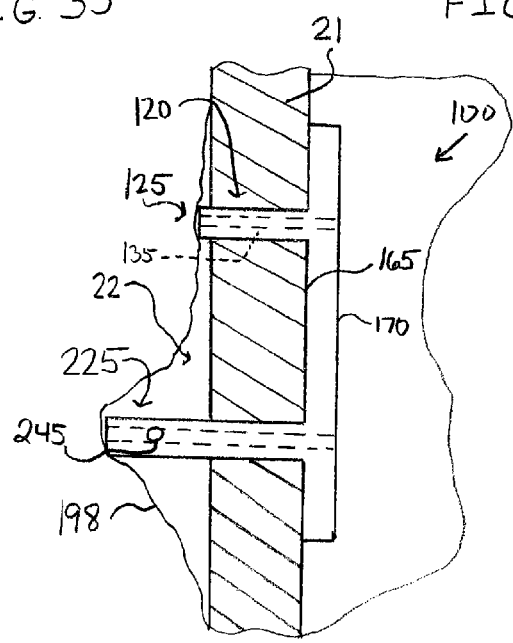
FIG. 35 is a cross sectional view of the trabecular meshwork with the device with an expandable member in a first position.
Figure 36:
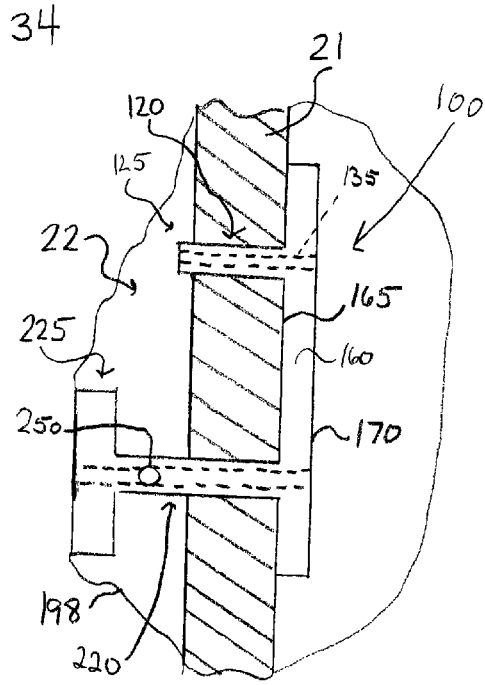
FIG. 36 is a cross sectional view of the trabecular meshwork with the device of FIG. 35 with the expandable member in a second expanded position.

As shown in FIGS. 35 and 36, the first end 225 of the second member 220 may be comprised of a material, including, but not limited to nitinol, that is capable of expanding (FIG. 36) when inserted in the Schlemm's canal 22. As best shown in FIGS. 21A through 21C, body 160 includes first and third openings 180 and 280 for fluidic communication with the first chamber 105, second and fourth openings 175 and 275 for fluidic communication with the first and second members 120 and 220 respectively, a first fluid passage 163 providing for fluid communication between the first and second openings 180 and 175 and a second fluid passage 263 providing for fluid communication between the third and fourth openings 280 and 275. The first member 120 includes a first opening 145 near a first end 125 of the first member for fluidic communication with the second chamber 110, a second opening 150 near a second end 130 of the first member for fluidic communication with the second opening 175 of the body 160, and a fluid passage 135 providing for fluidic communication between the openings 145 and 150. The second member 220 includes a first opening 245 near a first end 225 of the second member for fluidic communication with the second chamber 110, a second opening 250 near a second end 230 of the second member for fluidic communication with the fourth opening 275 of the body, and a fluid passage 235 providing for fluidic communication between the openings 245 and 250.

As shown in FIGS. 22 through 32, a plurality of members 120 may be provided having a first end 125 extending outward from the body 160. It is to be understood that the members 120 may extend substantially perpendicularly outward from the body 160, at angles other than substantially perpendicularly outward from the body 160, and combinations thereof. The members 120 may extend parallel to each other or at different angles. One or more members 120 may have a different length or extend farther from the body 160 than other members 120. In a non-limiting example, the members 120 may all have different lengths or extend from the body 160 different lengths. The members 120 may be provided in one or more substantially planar rows, rows and columns, in an array, or randomly extending from the body 160.

It is to be understood that one or more of the apertures 145, 150, 175, 180 and passages 135 and 163 of the members 120 and the body 160 may be plugged with a dissolvable material. In a non-limiting example, the material may be a bioabsorbable material. In a non-limiting example, the material may be a material capable of absorbing when energy is applied to the material, including, but not limited to radio frequency and laser energy. It is to be understood that the energy may be applied to the material non-invasively. In a non-limiting example, energy may be applied (such as by an ophthalmologist) to dissolve some or all of the absorbable material to selectively increase the fluid flow from the anterior chamber 20 to the Schlemm's canal 22. It is to be understood that one or more members 120 may be plugged with a bioabsorbable material and one or more members 120 may be plugged with a material absorbable when energy is applied to it.

Figure 22A:
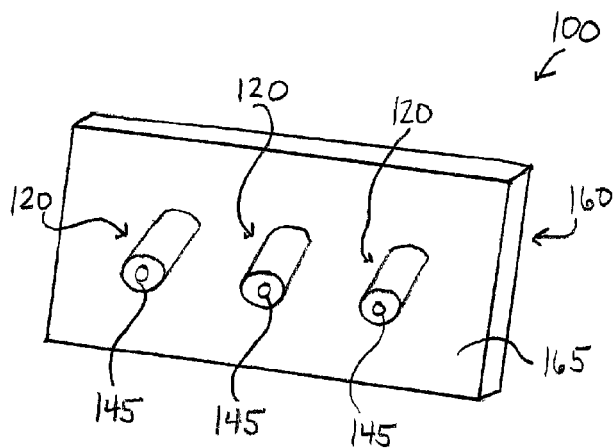
FIG. 22A is a perspective view of the device with a plurality of members.
Figure 22B:
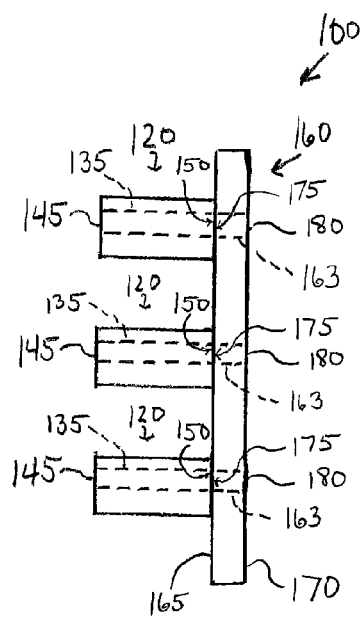
FIG. 22B is an overhead view of the device of FIG. 22A.
Figure 22C:
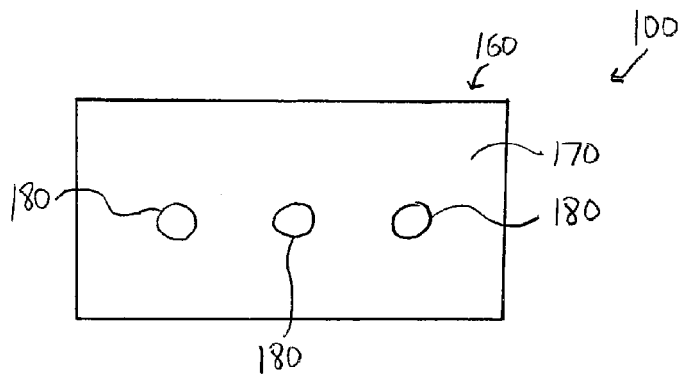
FIG. 22C is a rear view of the device of FIG. 22A.
Figure 23A:
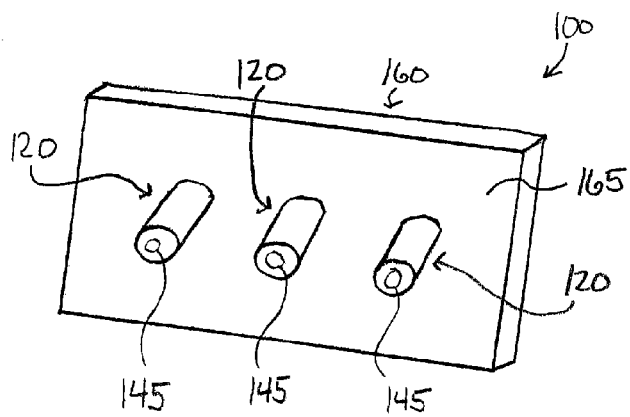
FIG. 23A is a perspective view of the device with a plurality of members.
Figure 23B:
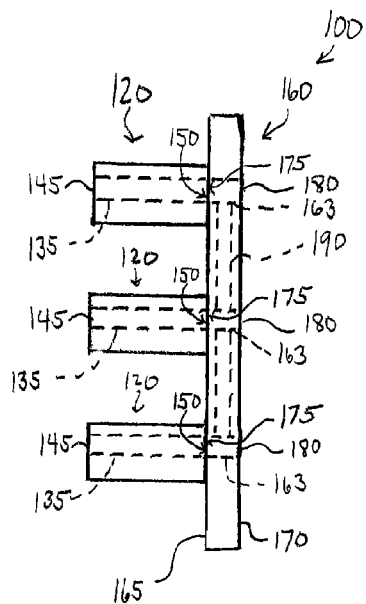
FIG. 23B is an overhead view of the device of FIG. 23A.
Figure 23C:
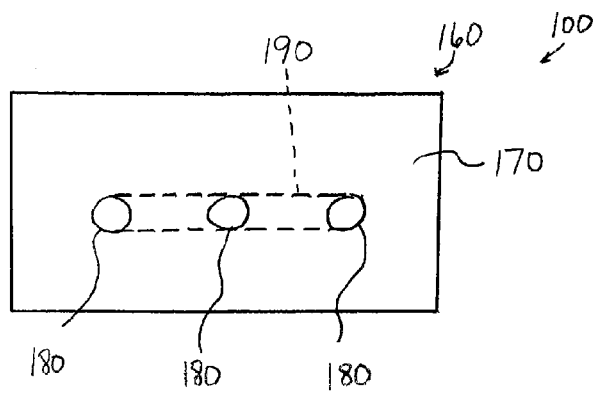
FIG. 23C is a rear view of the device of FIG. 23A.
Figure 24A:
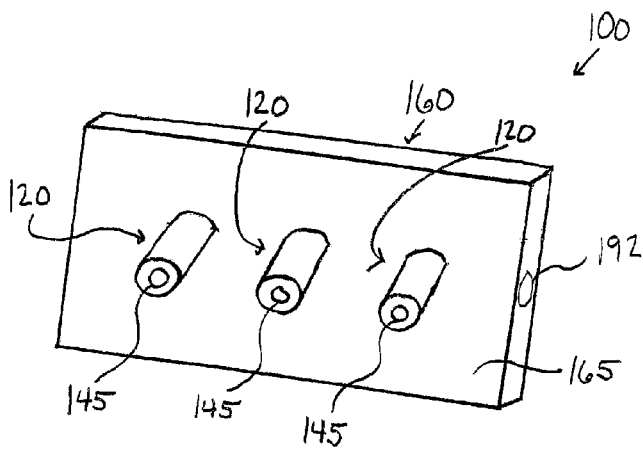
FIG. 24A is a perspective view of the device with a plurality of members.
Figure 24B:
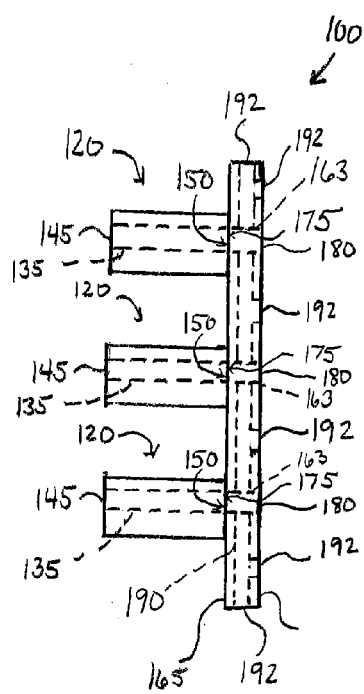
FIG. 24B is an overhead view of the device of FIG. 24A.
Figure 24C:
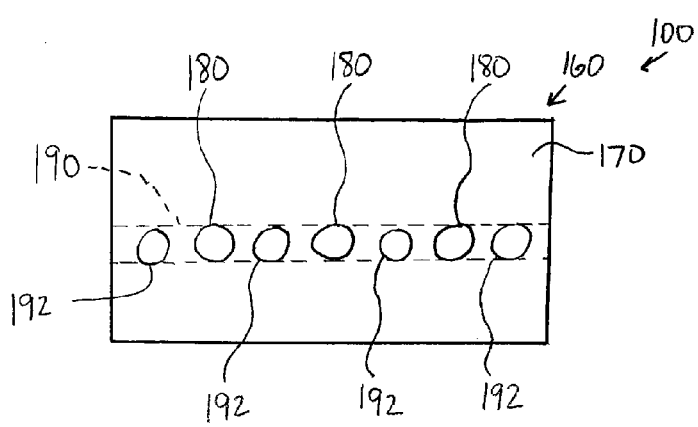
FIG. 24C is a rear view of the device of FIG. 24A.

As best shown in FIGS. 22A, 22B, and 22C, the members 120 may be provided in a substantially planar arrangement and the passages 135 and apertures 145 and 150 may be coaxially aligned with the passages 163 and apertures 175 and 180. As shown in FIG. 23B, the body 160 may be substantially hollow and have a cavity 190 in fluid communication with each of the passages 163. As shown in FIGS. 24B and 24C, the body 160 may be provided with one or more apertures 192 in fluid communication with the cavity 190.

Figure 25A:
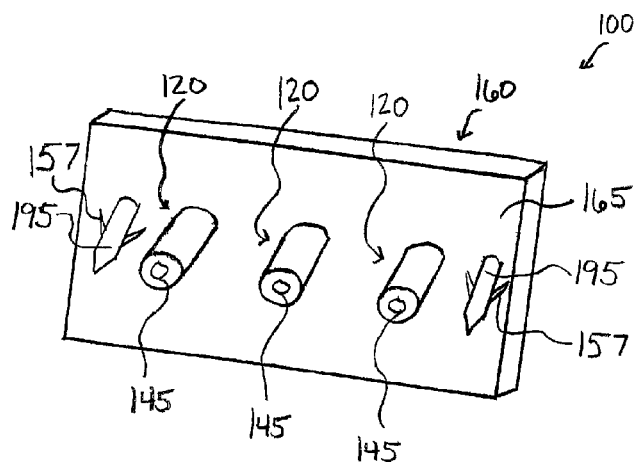
FIG. 25A is a perspective view of the device with a plurality of members.
Figure 25B:
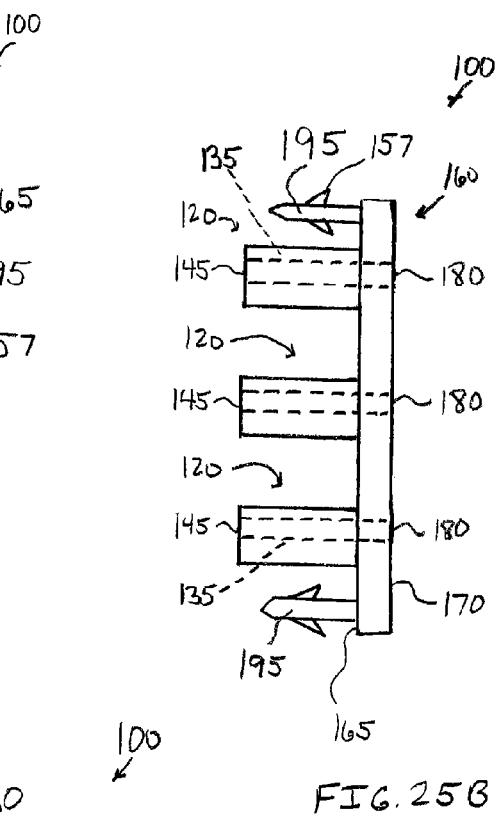
FIG. 25B is an overhead view of the device of FIG. 25A.
Figure 25C:
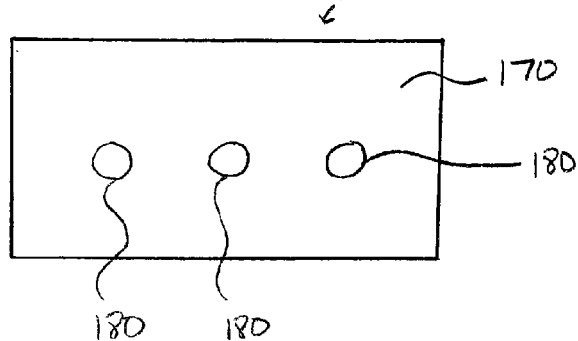
FIG. 25C is a rear view of the device of FIG. 25A.
Figure 26A:
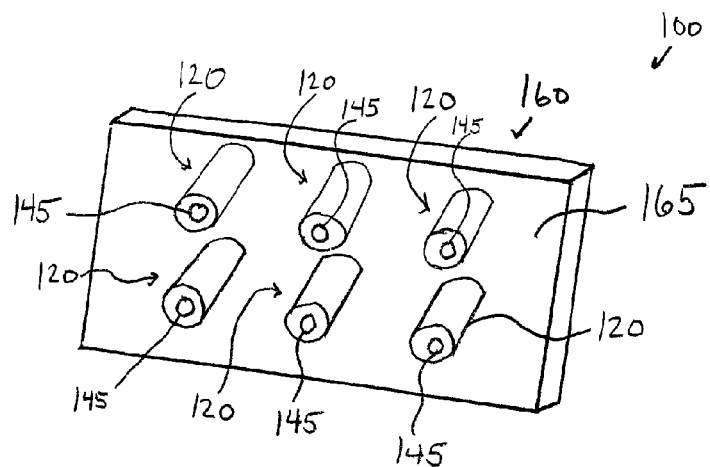
FIG. 26A is a perspective view of the device with a plurality of members.
Figure 26B:
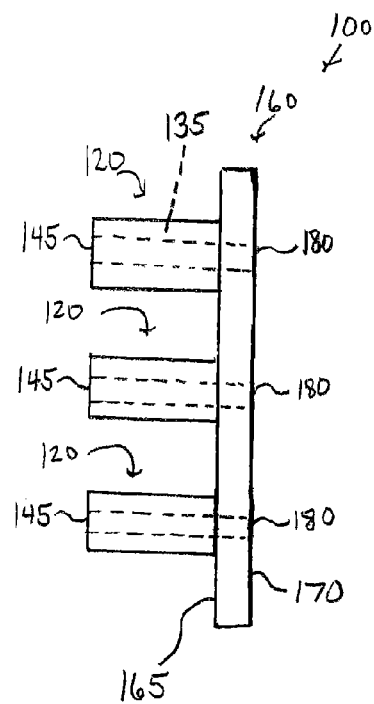
FIG. 26B is an overhead view of the device of FIG. 26A.
Figure 26C:
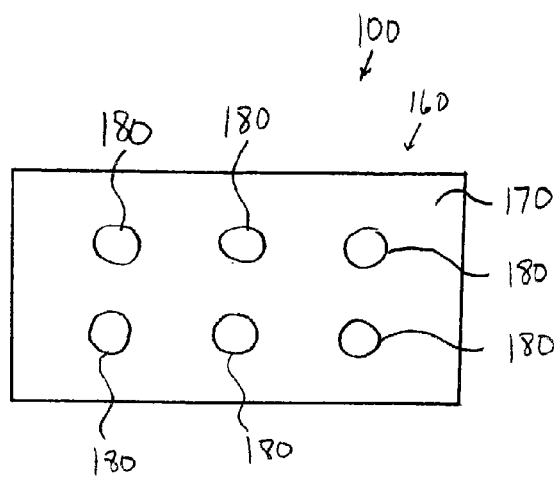
FIG. 26C is a rear view of the device of FIG. 26C.
Figure 27A:
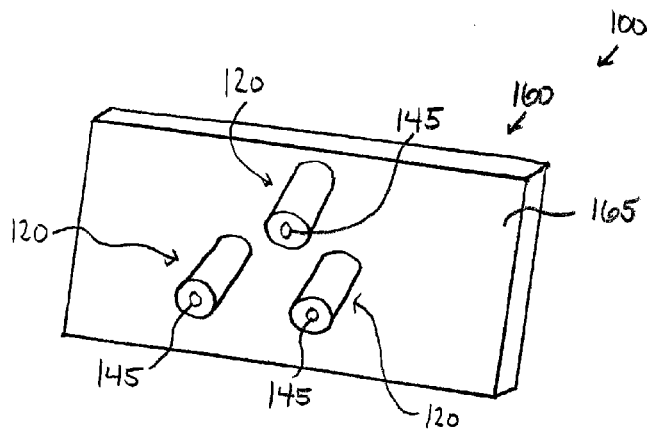
FIG. 27A is a perspective view of the device with a plurality of members.
Figure 27B:
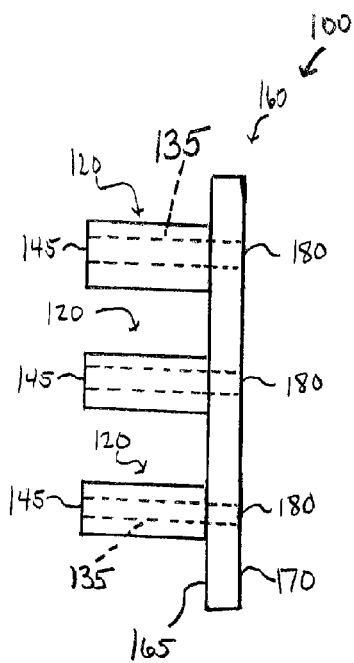
FIG. 27B is an overhead view of the device of FIG. 27A.
Figure 27C:
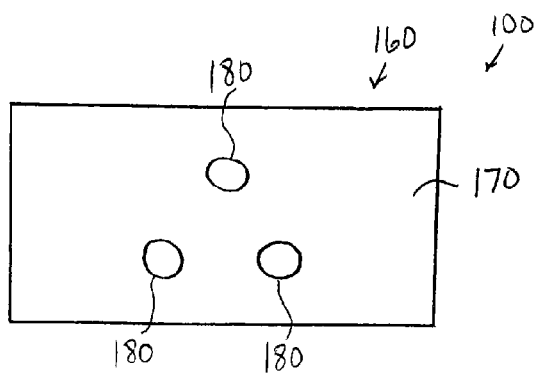
FIG. 27C is a rear view of the device of FIG. 27A.
Figure 28:
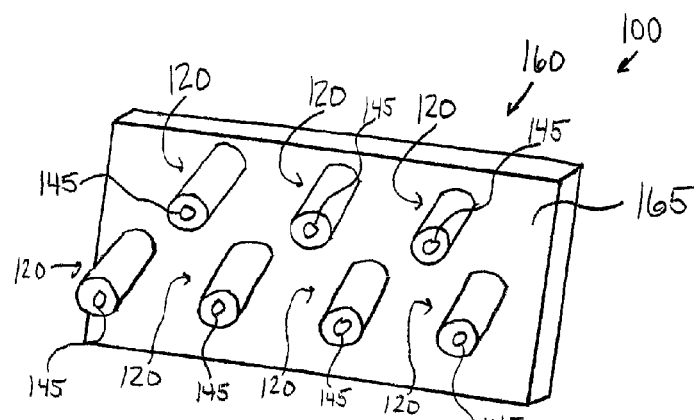
FIG. 28A is a perspective view of the device with a plurality of members.
FIG. 28B is an overhead view of the device of FIG. 28A.
FIG. 28C is a rear view of the device of FIG. 28A.
Figure 28:
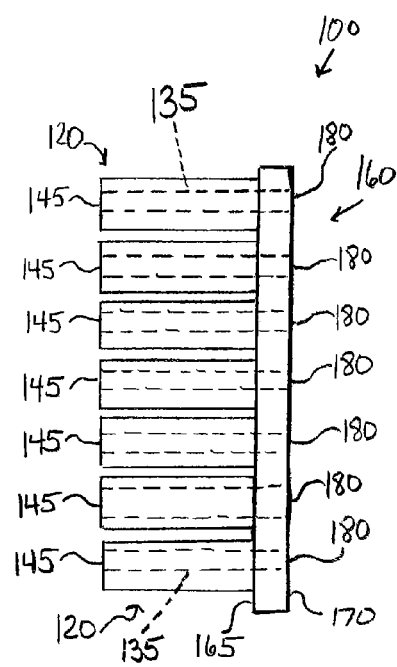
Figure 28:
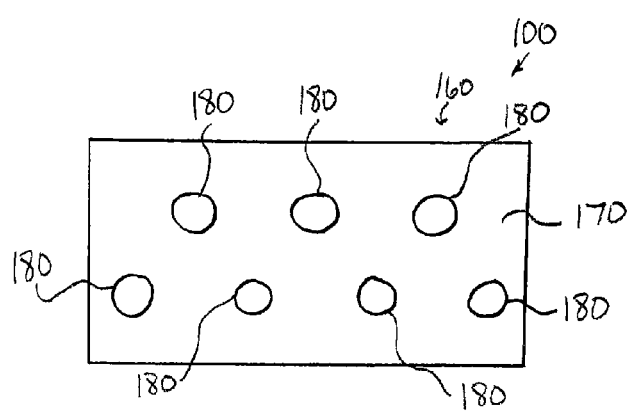

As best shown in FIGS. 25A and 25B one or more arms 195 having tissue engagers 157 may be provided for securing the device 100 to the tissue 115. Although shown as extending substantially perpendicularly outward from the body 160, it is to be understood that the arm 195 may extend at any angle from the body 160. It is also to be understood that the arm 195 may be positioned anywhere on the body 160. In a non-limiting example, the arm 195 may extend through the tissue 115 to engage, for example, the walls 198 of the Schlemm's canal 22 or the schlera 11. In a non-limiting example, the arm 195 may be a screw.

As shown in FIGS. 26A, 26B, 26C, 28A, 28B and 28C, the members 120 may be provided in rows and columns. The rows and columns may extend outward from the body 160 in substantially planar rows and columns. It is to be understood that the rows and columns may comprise any number of members 120. As shown in FIGS. 27A, 27B, 27C, 28A, 28C, and 28C the members 120 or rows of the members 120 may be staggered. Although not shown, the members 120 may be positioned randomly on the body 160.

Figure 29A:
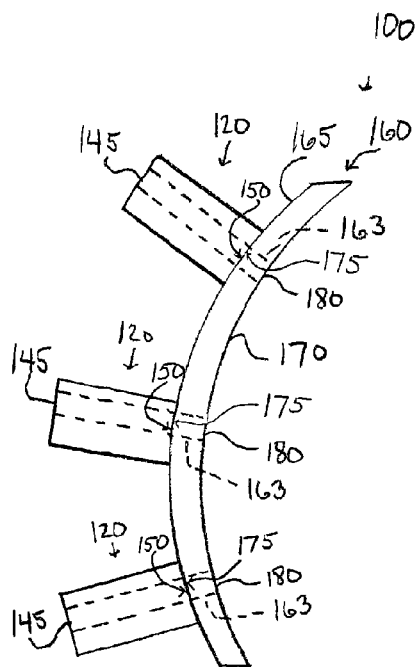
FIG. 29A is a side view of the device with a plurality of members and a body curved along the length $L_{C1}$.
Figure 29B:
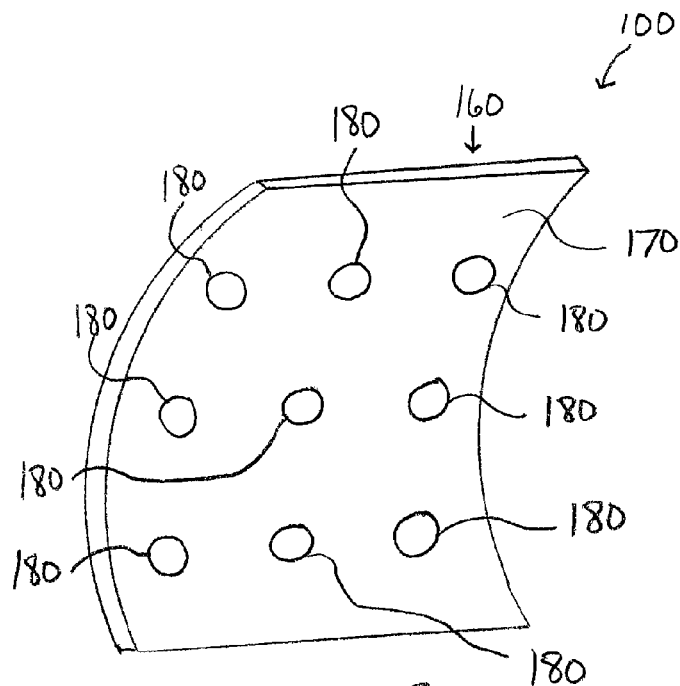
FIG. 29B is a rear view of the device of FIG. 29A.
Figure 29C:
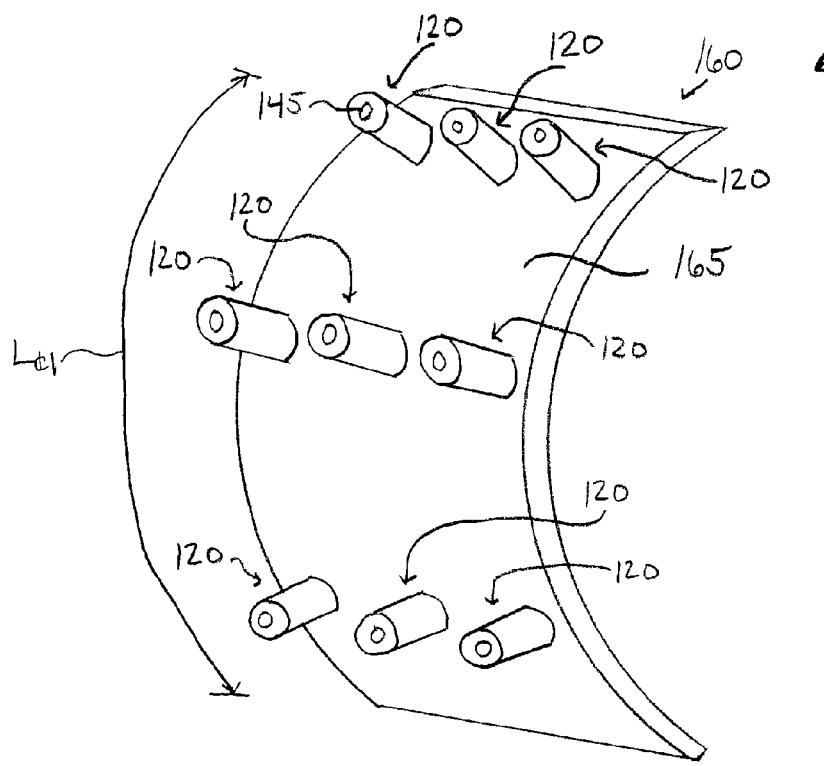
FIG. 29C is a frontal view of the device of FIG. 29A.
Figure 30A:
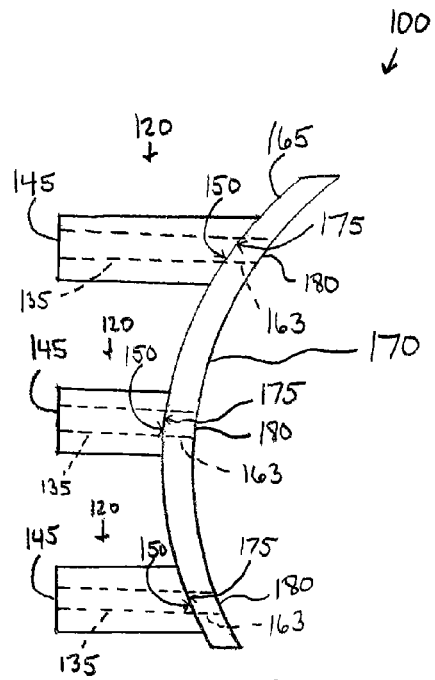
FIG. 30A is a side view of the device with a plurality of members and a body curved along the length $L_{C1}$.
Figure 30B:
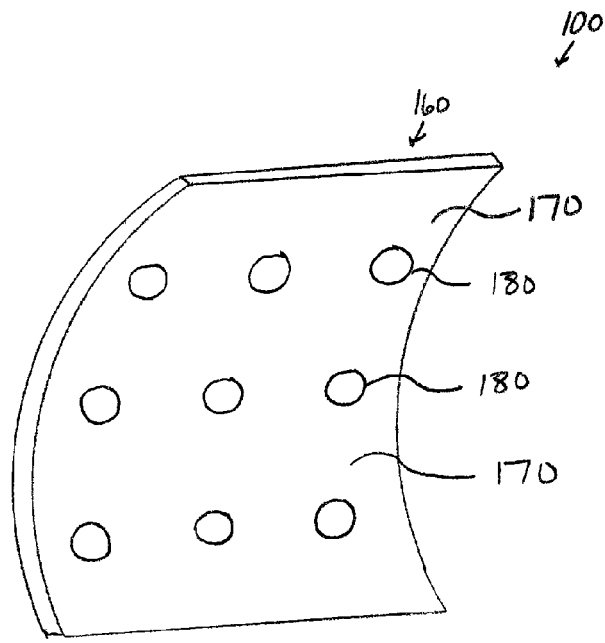
FIG. 30B is a rear view of the device of FIG. 30A.
Figure 30C:
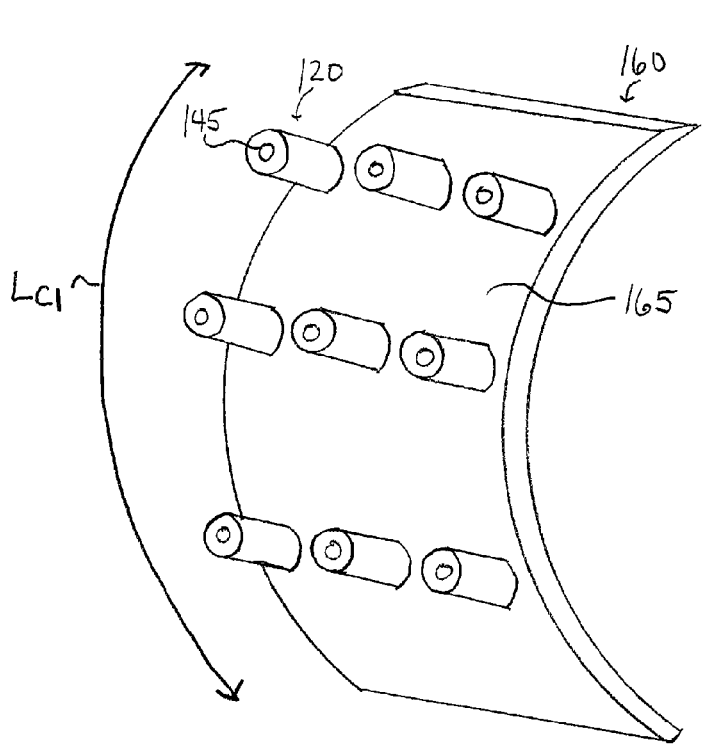
FIG. 30C is a frontal view of the device of FIG. 30A.

As shown in FIGS. 29A, 29B, 29C, 30A, 30B, and 30C, a plurality of members 120 may be provided extending outward from the side 165 having the curved length $L_{C1}$. As best shown in FIGS. 29A and 29C, the members 120 may extend substantially perpendicularly from the side 165. As best shown in FIGS. 30A and 30B, the members 120 may extend outward from the side 165 substantially parallel to each other.

Figure 31A:
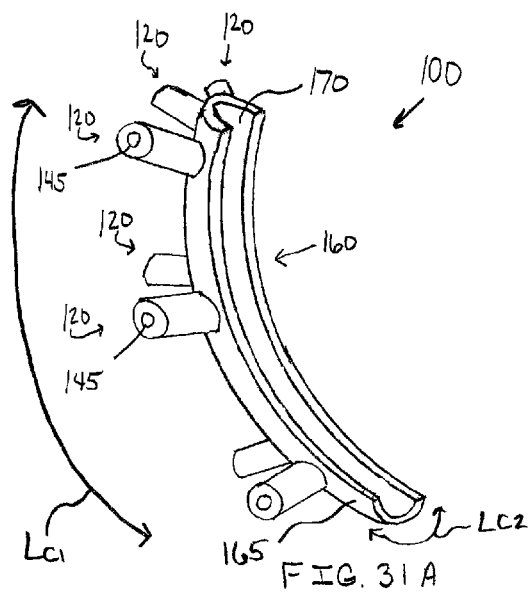
FIG. 31A is a side view of the device with a plurality of members and a body curved along the length $L_{C1}$ and the length $L_{C2}$.
Figure 31B:
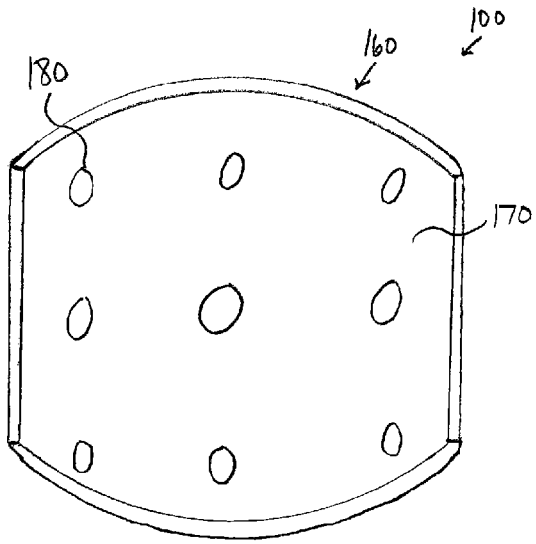
FIG. 31B is a rear view of the device of FIG. 31A.
Figure 31C:
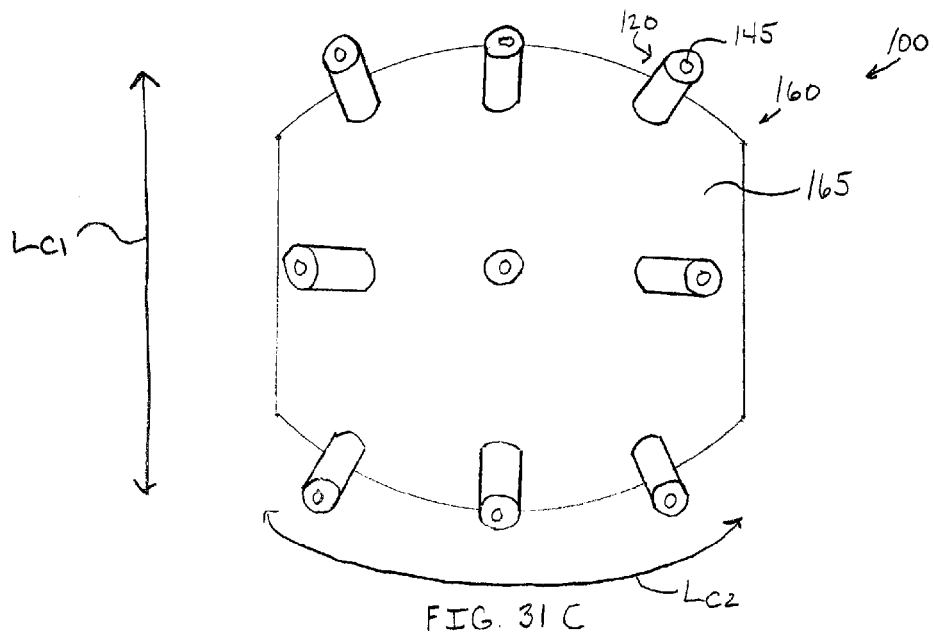
FIG. 31C is a frontal view of the device of FIG. 31A.

As shown in FIGS. 31A, 31B, and 31C, a plurality of members 120 may be provided extending outward from the side 165 of the body 160 having the curved length $L_{C1}$ and a curved length $L_{C2}$ in two different directions orthogonal to one another. As best shown in FIGS. 31A and 31C, the members 120 may extend substantially perpendicularly from the side 165. In a non-limiting example (not shown), the members 120 of a row or column may extend from the side 165 substantially parallel to each other. In yet another non-limiting example, all of the members 120 may extend outward from the side 165 substantially parallel to each other.

Figure 32A:
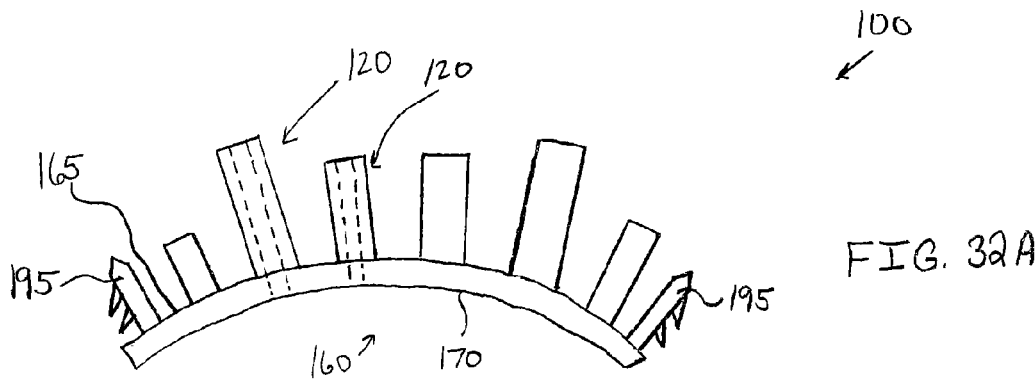
FIG. 32A is an overhead view of the device with a plurality of members.
Figure 32B:
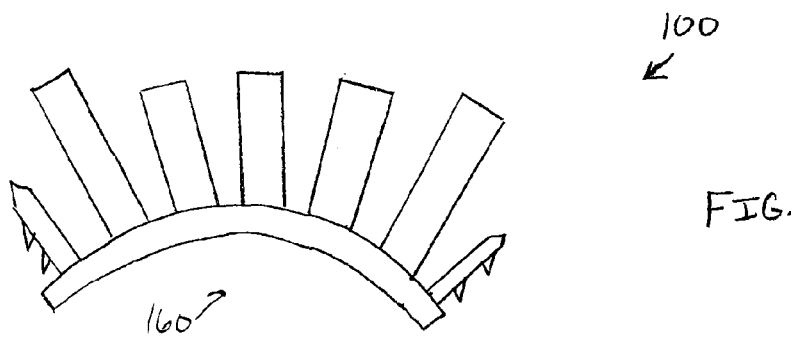
FIG. 32B is an overhead view of the device with a plurality of members.
Figure 32C:
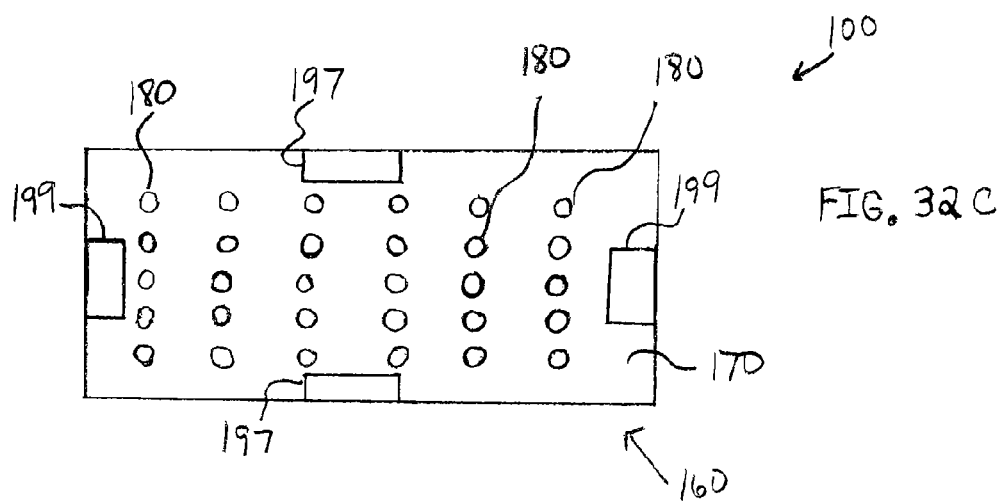
FIG. 32C is a rear view of the device of FIG. 32A.

In an illustrative example, as shown in FIGS. 32A, 32B, and 32C, a plurality of members 120 is provided extending from the body 160. The first end 125 of each member 120 may extend a different length than the other members 120. The device 100 may be provided with one or more arms 195 having one or more tissue engagers 157. The body 160 may be provided with one or more installation keys 199 (hereinafter referred to as "the key 199"). During implantation of the device 100, the device 100 may be gripped, engaged or otherwise manipulated by an implantation device (not shown) during insertion or positioning of the members 120 in the tissue 115. Although shown as substantially rectangular in shape, the key 199 may be provided in any shape, including, but not limited to a protuberance, an indentation, an aperture, and combinations thereof.

Figures 37A, 37B:
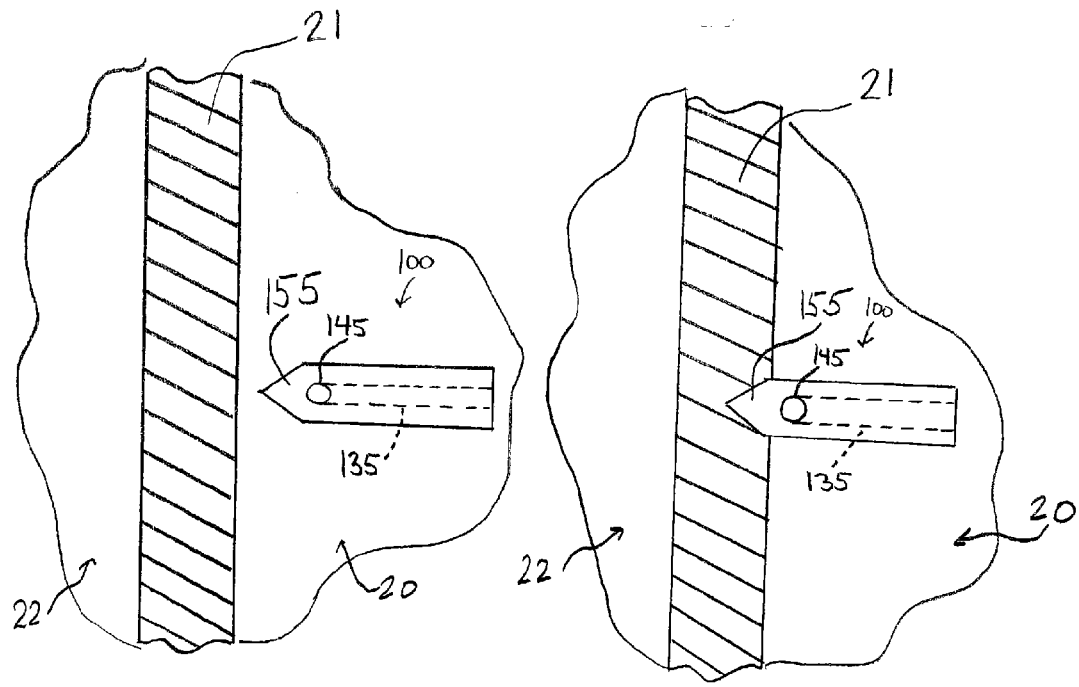
FIG. 37A is a cross sectional view of the trabecular meshwork and a side view of the device prior to insertion in the trabecular meshwork.
FIG. 37B is a side view of the device of FIG. 37A during insertion through the trabecular meshwork.
Figures 37C, 37D:
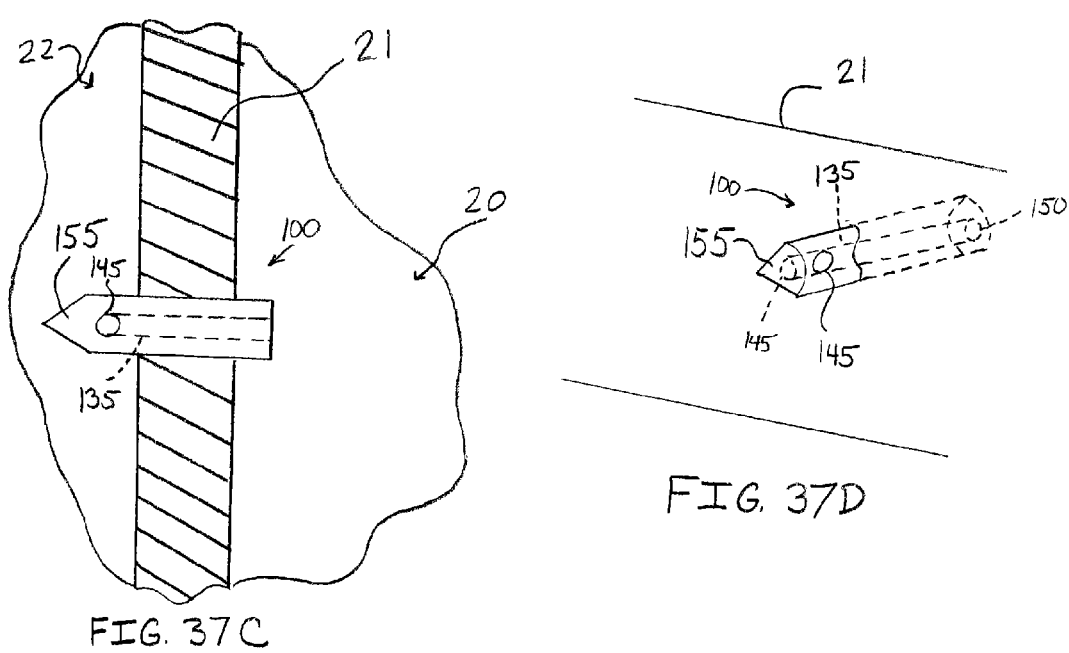
FIG. 37C is a side view of the device of FIG. 37A with the passage in fluid communication with the anterior chamber and the Schlemm's canal.
FIG. 37D is a perspective view of the device of FIG. 37C.
Figure 37E:
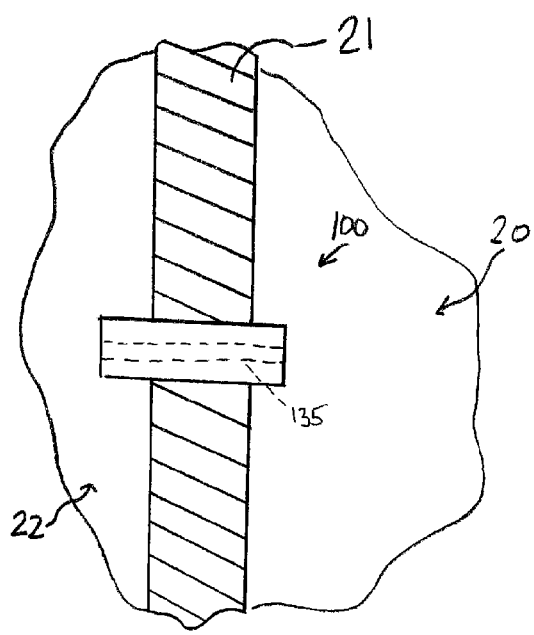
FIG. 37E is a side view of the device of FIG. 37C with a dissolvable head.
Figure 37F:
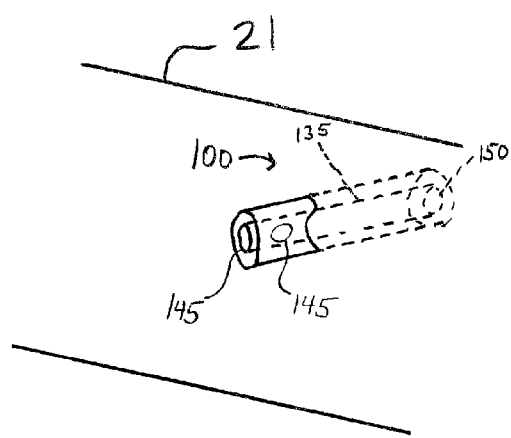
FIG. 37F is a perspective view of the device of FIG. 37E.

Turning to the device 100, an example of how to use the device 100 as illustrated in FIGS. 1, and 4-39 is set forth below. The device 100 may be inserted through the tissue 115 with or without preparing a channel or canal therethrough prior to positioning of the member 120 in the tissue 115. As shown in FIG. 37A, 37B, and 37C, the member 120 may be inserted through the trabecular meshwork 21 without preparing a channel therethrough. As shown in FIG. 37B, the head 155 may pierce the trabecular meshwork 21 to place the passage 135 in fluid communication with the anterior chamber 20 and the Schlemm's canal 22 as shown in FIG. 37C. As shown in FIGS. 37D, 37E, and 37F, the head 155 may be comprised of a dissolvable material that may dissolve after a predetermined time or after the application of energy to provide fluid access (or additional fluid access) to the passage 135.

Figure 39A:
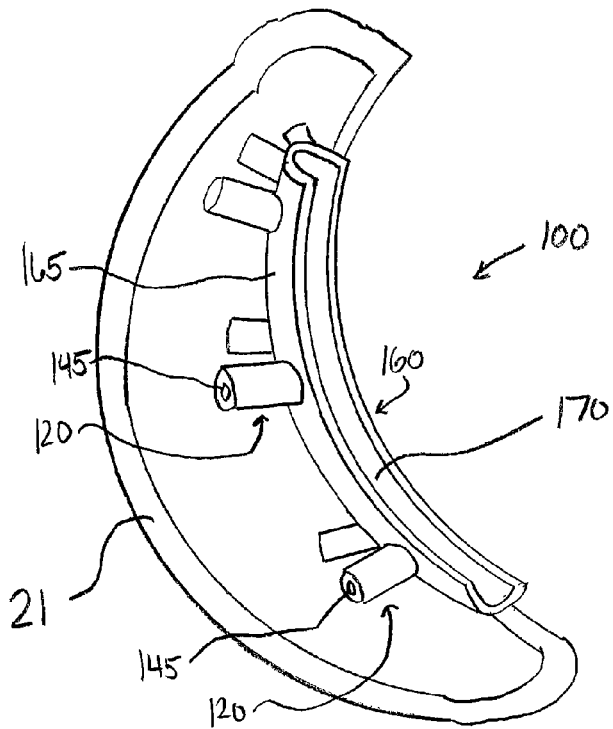
FIG. 39A is a cross sectional view of the trabecular meshwork and a side view of the device having a plurality of members and the body curved along the length $L_{C1}$ and along the length $L_{C2}$ prior to insertion of the members in the trabecular meshwork.
Figure 39B:
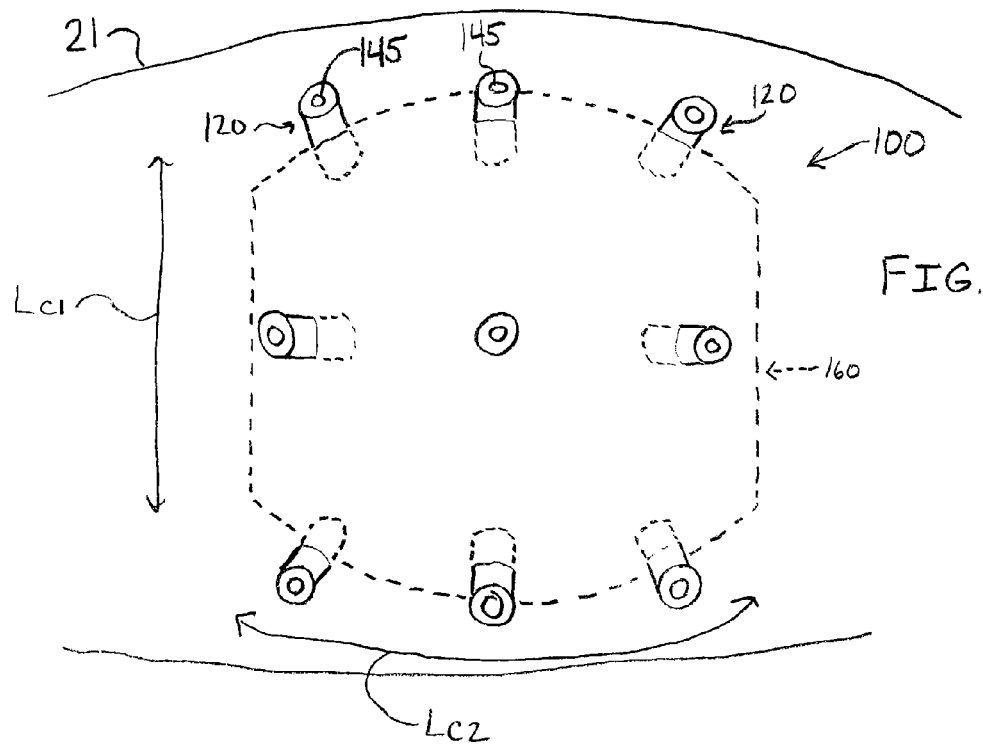
FIG. 39B is a frontal view of the device of FIG. 39A with the passages in fluid communication with the anterior chamber and the Schlemm's canal.
Figure 39C:
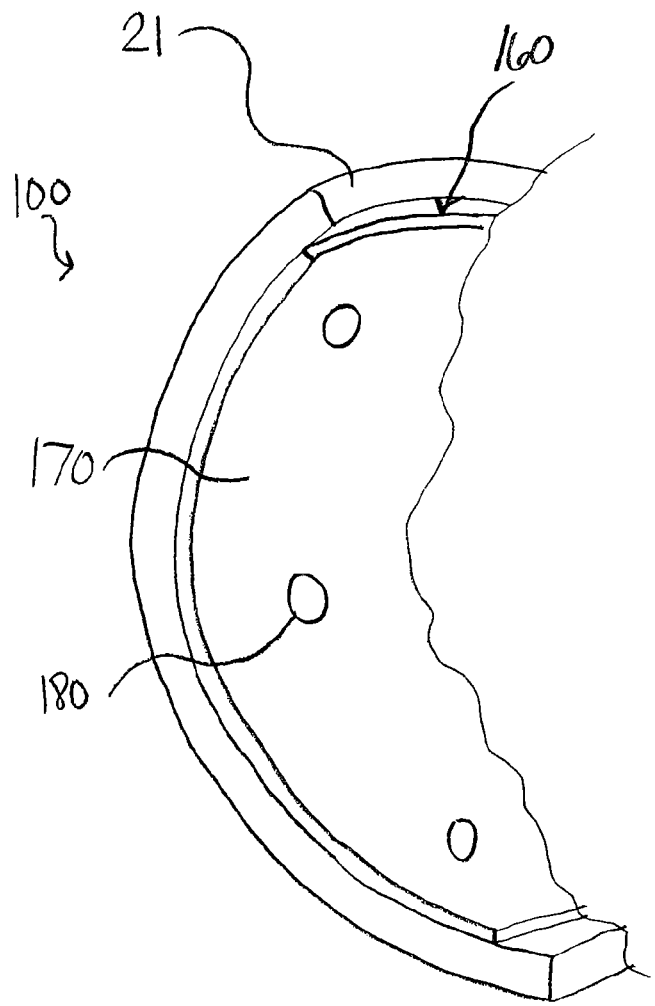
FIG. 39C is a rear perspective view of a portion of the device of FIG. 39B.

As shown in FIG. 39A, a device 100 provided with a plurality of members 120 may be positioned in the trabecular meshwork 21 with or without providing channels therein prior to insertion of the members 120. As shown in FIG. 39B, the members 120 may be positioned in the trabecular meshwork 21 to provide fluid flow between the anterior chamber 20 and the Schlemm's canal 22 via the passage 135. As shown in FIG. 39C, the body 160 may be shaped to conform the shape of the trabecular meshwork 21.

Although not shown, it is to be understood that any of the apertures 145, 150, 175, 180 or passage 135, and any combination thereof, may be coated or otherwise plugged with a dissolvable material capable of dissolving at a predetermined time or upon the application of energy thereto to allow fluid flow therethrough. In a non-limiting example, a plurality of members 120 has any of their respective apertures 145, 150, 175, 180 or passage 135, and any combination thereof plugged with a material capable of dissolving upon the application of energy thereto to allow fluid flow therethrough.

The volumetric flow rate of fluid from the anterior chamber 20 may be selectively increased to maintain the pressure in the anterior chamber 20 by dissolving the material in one or more members through the application of energy thereto. Such selective dissolving of the material is useful to non-invasively calibrate or otherwise maintain the fluid flow of the device 100 due, for example, to the plugging of the passages 135 of other members 120 from tissue, blood, or other matter.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A fluid communication device configured to provide fluid flow between first and second chambers separated by tissue, the device including:
    a body configured to engage the tissue, the body including first and third openings for fluidic communication with the first chamber, second and fourth openings for fluidic communication with first and second members respectively, a first fluid passage providing for fluidic communication between the first and second openings and a second fluid passage providing for fluidic communication between the third and fourth openings;
    the first and second members extending from the body and being configured to be inserted through the tissue;
    the first member including a first opening near a first end of the member for fluidic communication with the second chamber, a second opening near a second end of the first member for fluidic communication with the second opening of the body, and a fluid passage providing for fluidic communication between the openings;
    the second member including a first opening near a first end of the second member for fluidic communication with the second chamber, a second opening near a second end of the second member for fluidic communication with the fourth opening of the body, and a fluid passage providing for fluidic communication between the openings; and
    a head extending from the first end of one of the first or second members, the head being configured to be insertable through the tissue, wherein the second member is greater in length than the first member, and wherein the second member is configured to support a wall of the second chamber to maintain the second chamber in an open position relative to the first member thereby allowing for unimpeded flow of fluid from the first chamber to the second chamber via the first member.

2. A fluid communication device according to claim 1, further including at least one tissue engager extending from the body, the at least one tissue engager being configured to secure the device to the tissue.

3. A fluid communication device according to claim 1, wherein the head comprises a dissolvable material that is dissolvable to provide additional fluid access to the fluid passage of the first member.

4. A fluid communication device according to claim 1, wherein the body is curved to substantially conform to the shape of the tissue.

5. A fluid communication device according to claim 1, wherein the first end of the second member comprises an expandable material that is configured to expand after the second member has been inserted through the tissue and into the second chamber.

6. A fluid communication device according to claim 5, wherein the second member includes at least one opening disposed along its length, the at least one opening being in fluidic communication with the fluid passage of the second member.

7. A fluid communication device configured to provide fluid flow between first and second chambers separated by tissue, the device including:
  a body configured to engage the tissue, the body including a first opening for fluidic communication with the first chamber, a second opening for fluidic communication with at least one member, and a fluid passage providing for fluidic communication between the openings;
  the at least one member extending from the body and being configured to be inserted through the tissue, the at least one member including a first opening near a first end of the member for fluidic communication with the second chamber, a second opening near a second end of the member for fluidic communication with the second opening of the body, and a fluid passage providing for fluidic communication between the openings; and
  a head extending from the first end of the member, the head being configured to be insertable through the tissue, wherein the at least one member includes at least one opening disposed along its length, the at least one opening being in fluidic communication with the fluid passage of the at least one member, and wherein the fluid passage of the at least one member extends longitudinally along an outer circumference of the at least one member.

8. A fluid communication device according to claim 7, wherein the fluid passage in the at least one member is a channel extending longitudinally along the outer circumference of the at least one member.

9. A fluid communication device according to claim 7, wherein a plurality of circumferentially spaced channels extend longitudinally along the outer circumference of the at least one member.

10. A method of installing a fluid communication device to provide for fluid flow from an anterior chamber of an eye to Schlemm's canal through trabecular meshwork of the eye, the device including a body having first and third openings for fluidic communication with the anterior chamber, second and fourth openings for fluidic communication with first and second members respectively, a first fluid passage providing for fluidic communication between the first and second openings and a second fluid passage providing for fluidic communication between the third and fourth openings, the first member including a first opening near a first end of the first member for fluidic communication with the Schlemm's canal, a second opening near a second end of the first member for fluidic communication with the second opening of the body, and a fluid passage providing for fluidic communication between the openings, the second member including a first opening near a first end of the second member for fluidic communication with the Schlemm's canal, a second opening near a second end of the second member for fluidic communication with the fourth opening of the body, and a fluid passage providing for fluidic communication between the openings, and a head extending from the first end of one of the first or second members, the head being configured to be insertable through the trabecular meshwork, the method including:
  advancing the fluid communication device through the anterior chamber toward the trabecular meshwork;
  inserting the fluid communication device into the trabecular meshwork by piercing the trabecular meshwork with the head; and
  advancing the fluid communication device through the trabecular meshwork toward the Schlemm's canal until the body abuts a wall of the trabecular meshwork in the anterior chamber and the first and second members are inserted through the trabecular meshwork, wherein
  the second member is greater in length than the first member, and the second member is configured to support a wall of the Schlemm's canal to maintain the Schlemm's canal in an open position relative to the first member thereby allowing for unimpeded flow of fluid from the anterior chamber to the Schlemm's canal via the first member.

11. A method according to claim 10, wherein the body includes at least one installation key engagable by an implantation device to install the fluid communication device.

12. A fluid communication device configured to provide fluid flow between first and second chambers separated by tissue, the device including:
  a body configured to engage the tissue, the body including a first opening for fluidic communication with the first chamber, a second opening for fluidic communication with at least one member, and a fluid passage providing for fluidic communication between the openings;
  the at least one member extending from the body and being configured to be inserted through the tissue;
  the at least one member including a first opening near a first end of at least one member for fluidic communication with the second chamber, a second opening near a second end of the at least one member for fluidic communication with the second opening of the body, and a fluid passage providing for fluidic communication between the openings; and
  a head extending from the first end of the at least one member, the head being configured to be inserted through the tissue; wherein the first end of the at least one member comprises an expandable material that is configured to expand after the at least one member has been inserted through the tissue and into the second chamber.

13. A fluid communication device according to claim 12, wherein the at least one member includes at least one opening disposed along its length, the at least one opening being in fluidic communication with the fluid passage of the at least one member.

14. A fluid communication device configured to provide fluid communication between first and second chambers separated by tissue, the device including:
  a body having a curved length to substantially conform to the shape of the tissue, and a plurality of spaced apart members extending outwardly from the curved body, the members being configured to be inserted through the tissue, the body and the members having aligned passages providing for fluidic communication between the first and second chambers through the aligned passages when the members are inserted through the tissue; and
  a head extending from an outer end of at least one of the members, the head being configured to be insertable through the tissue, wherein some of the members are longer than other of the members, and wherein the longer members are configured to support a wall of the second chamber to maintain the second chamber in an open position relative to the other members thereby allowing for unimpeded flow of fluid from the first chamber to the second chamber via the other members.

15. A fluid communication device according to claim 14, wherein the members extend perpendicularly from the curved length of the body.

16. A fluid communication device according to claim 14, further comprising at least one tissue engager extending from the body, the at least one tissue engager being configured to secure the device to the tissue.

17. A fluid communication device according to claim 14, wherein the body is curved in two different directions orthogonal to one another.

* * * * *